US011549083B2

United States Patent
Man et al.

(10) Patent No.: US 11,549,083 B2
(45) Date of Patent: Jan. 10, 2023

(54) USE OF PROPOXYLATED SURFACTANT OR POLYMER IN FOAMING APPLICATIONS TO CONTROL VISCOELASTICITY IN HIGHLY ACTIVE LIQUID FORMULATIONS

(71) Applicant: ECOLAB USA INC., Saint Paul, MN (US)

(72) Inventors: Victor Fuk-Pong Man, Saint Paul, MN (US); Derrick Richard Anderson, Saint Paul, MN (US); Amanda R. Blattner, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 0 days.

(21) Appl. No.: 17/446,631

(22) Filed: Sep. 1, 2021

(65) Prior Publication Data

US 2022/0017842 A1    Jan. 20, 2022

Related U.S. Application Data

(60) Division of application No. 16/855,158, filed on Apr. 22, 2020, now Pat. No. 11,136,533, which is a
(Continued)

(51) Int. Cl.
*C11D 1/83* (2006.01)
*C11D 3/37* (2006.01)
(Continued)

(52) U.S. Cl.
CPC .......... *C11D 3/3707* (2013.01); *A01N 25/16* (2013.01); *A01N 25/30* (2013.01); *A61K 8/463* (2013.01);
(Continued)

(58) Field of Classification Search
CPC ....... C11D 17/041; C11D 3/3765; C11D 3/39; C11D 11/0023; C11D 3/3723; C11D 1/72; C11D 3/381; C11D 1/722; A61K 2300/00
See application file for complete search history.

(56) References Cited

U.S. PATENT DOCUMENTS 5,167,872 A    12/1992    Pancheri et al.
5,480,586 A    1/1996    Jakubicki et al.
(Continued)

FOREIGN PATENT DOCUMENTS

CN    105121617 A    12/2015
CN    105473697 A    4/2016
(Continued)

OTHER PUBLICATIONS

BASF The Chemical Company, "Lutensol XP & Lutensol XL: Nonionic Surfactants for Household and I&I Cleaners Formulations", 4 pages, Dec. 2005.
(Continued)

*Primary Examiner* — John R Hardee
(74) *Attorney, Agent, or Firm* — McKee, Voorhees & Sease, PLC

(57) ABSTRACT

Antimicrobial or non-antimicrobial compositions, sanitizing compositions and other compositions combining use of a propoxylated EO/PO block copolymer surfactant and/or propoxylated polymer in combination with at least one additional anionic and/or nonionic surfactant to provide concentrated compositions having a desired viscoelasticity at an active level of at least 18% are disclosed. Non-antimicrobial applications combining use of a propoxylated surfactant and/or propoxylated polymer in combination with at least one additional anionic and/or nonionic surfactant to provide compositions having a desired viscoelasticity are also disclosed. Methods of using concentrated and use
(Continued)

compositions having desired foaming enhancement and stabilization are also disclosed.

17 Claims, 4 Drawing Sheets

Related U.S. Application Data continuation of application No. 16/143,060, filed on Sep. 26, 2018, now Pat. No. 10,662,396.

(60) Provisional application No. 62/564,122, filed on Sep. 27, 2017.

(51) Int. Cl.

| | | |
|---|---|---|
| *C11D 3/48* | (2006.01) | |
| *A61Q 19/10* | (2006.01) | |
| *A61K 8/86* | (2006.01) | |
| *A61K 8/90* | (2006.01) | |
| *A01N 25/16* | (2006.01) | |
| *A61Q 17/00* | (2006.01) | |
| *A61K 8/46* | (2006.01) | |
| *A61K 8/60* | (2006.01) | |
| *A01N 25/30* | (2006.01) | |

(52) U.S. Cl.
CPC ............ *A61K 8/604* (2013.01); *A61K 8/86* (2013.01); *A61K 8/90* (2013.01); *A61Q 17/005* (2013.01); *A61Q 19/10* (2013.01); *C11D 3/48* (2013.01)

(56) References Cited

U.S. PATENT DOCUMENTS

| | | | |
|---|---|---|---|
| 5,753,605 A * | 5/1998 | Blatter | C11D 3/2037 510/342 |
| 5,780,417 A | 7/1998 | Gorlin | |
| 5,912,222 A | 6/1999 | Thomas et al. | |
| 5,993,562 A * | 11/1999 | Roelofs | B08B 9/057 134/22.16 |
| 6,010,996 A | 1/2000 | Hu et al. | |
| 6,136,769 A | 10/2000 | Asano et al. | |
| 6,224,685 B1 | 5/2001 | Gross et al. | |
| 6,274,539 B1 | 8/2001 | Kacher et al. | |
| 6,339,054 B1 | 1/2002 | Levitt et al. | |
| 6,350,725 B1 | 2/2002 | Levitt et al. | |
| 6,387,870 B1 | 5/2002 | Klaers et al. | |
| 6,458,753 B1 | 10/2002 | Haylett | |
| 6,506,261 B1 | 1/2003 | Man | |
| 6,506,717 B1 | 1/2003 | Kott et al. | |
| 6,602,350 B2 | 8/2003 | Levitt et al. | |
| 6,617,303 B1 | 9/2003 | Smith et al. | |
| 6,786,223 B2 | 9/2004 | Klinkhammer et al. | |
| 6,864,220 B2 | 3/2005 | Levitt et al. | |
| 6,878,681 B1 | 4/2005 | Gohl et al. | |
| 7,482,315 B2 | 1/2009 | Levitt et al. | |
| 7,951,245 B2 | 5/2011 | Levitt et al. | |
| 8,246,696 B2 | 8/2012 | Man et al. | |
| 8,697,622 B2 | 4/2014 | Man et al. | |
| 8,895,492 B2 | 11/2014 | Tarng et al. | |
| 9,034,813 B2 | 5/2015 | Man et al. | |
| 9,410,110 B2 | 8/2016 | Man et al. | |
| 9,862,913 B2 | 1/2018 | Hardy | |
| 10,000,728 B2 | 6/2018 | Goncalves Rodrigues | |
| 2002/0007519 A1 * | 1/2002 | Noyes | C11D 7/5013 8/142 |
| 2007/0275868 A1 | 11/2007 | Cooremans et al. | |
| 2013/0274167 A1 | 10/2013 | Gutowski et al. | |
| 2014/0148374 A1 | 5/2014 | Man et al. | |
| 2016/0157479 A1 | 6/2016 | Elliott et al. | |
| 2016/0201014 A1 | 7/2016 | Perez-Garcia et al. | |
| 2016/0312152 A1 | 10/2016 | Borne et al. | |
| 2017/0009189 A1 | 1/2017 | Rees et al. | |
| 2017/0015958 A1 | 1/2017 | Rodrigues | |
| 2018/0216037 A1 | 8/2018 | Hamersky et al. | |

FOREIGN PATENT DOCUMENTS

| | | | |
|---|---|---|---|
| EP | 0738778 A1 | 10/1996 | |
| EP | 1583813 B1 | 10/2005 | |
| JP | 62181399 A | 8/1987 | |
| JP | 62181400 A | 8/1987 | |
| JP | 2000515175 A | 11/2000 | |
| JP | 2009537692 A | 10/2009 | |
| JP | 2016505657 A | 2/2016 | |
| WO | 9728238 A1 | 8/1997 | |
| WO | 9844791 A1 | 10/1998 | |
| WO | 0119507 A1 | 3/2001 | |
| WO | 2008076693 A2 | 6/2008 | |

OTHER PUBLICATIONS

Huntsman Corporation, "Surfonic® L24-7 Surfactant", Technical Bulletin, pp. 1-2, 2007.

Boethling, Robert S., "Environmental Fate and Toxicity in Wastewater Treatment of Quaternary Ammonium Surfactants", Water Res., vol. 18, No. 9, pp. 1061-1076, Feb. 1984.

Tubajika, Kayimbi M., "Effectiveness of alkyl dimethyl benzyl ammonium chloride in reducing the population of Xanthomonas campetris pv. Vesicatoria and Pseudomonas syringae pv. syringae in tomatoes, beans, and peppers", Archives of Phytopathology and Plant Protection, pp. 688-697, Feb. 19, 2006.

Ecolab USA Inc., PCT/US2018/052946 filed Sep. 26, 2018, "International Search Report and the Written Opinion of the International Searching Authority or the Declaration", 17 pages, dated Nov. 20, 2018.

* cited by examiner

USE OF PROPOXYLATED SURFACTANT OR POLYMER IN FOAMING APPLICATIONS TO CONTROL VISCOELASTICITY IN HIGHLY ACTIVE LIQUID FORMULATIONS

CROSS-REFERENCE TO RELATED APPLICATIONS

This application is a Divisional Application of U.S. Ser. No. 16/855,158, filed Apr. 22, 2020, now U.S. Pat. No. 11,136,533 which is a Continuation Application of U.S. Ser. No. 16/143,060, filed Sep. 26, 2018, now U.S. Pat. No. 10,662,396, issued May 26, 2020, which claims priority under 35 U.S.C. § 119 to provisional application Ser. No. 62/564,122, filed Sep. 27, 2017, all of which are herein incorporated by reference in their entirety.

FIELD OF THE INVENTION

The present disclosure is related to compositions combining a propoxylated EO/PO block copolymer surfactant (and/or propoxylated polymers) with at least one additional anionic and/or nonionic surfactant to provide concentrated compositions having a desired viscoelasticity. The present disclosure is related to antimicrobial compositions and non-antimicrobial applications combining use of the propoxylated surfactant (and/or propoxylated polymers) in combination with at least one additional anionic and/or nonionic surfactant to provide concentrated compositions with actives of at least about 18% and having the desired viscoelasticity. In particular embodiments, the present disclosure provides compositions having desired foaming enhancement and methods employing the same for applications such as pot and pan cleaning, hand soaps, soaking compositions, and other soil removal applications with foam stabilization.

BACKGROUND OF THE INVENTION

Heavily soiled wares can require multiple cleaning steps to remove the soils from the surfaces of the wares. Pots and pans used for prepping, cooking, and baking ware in full service restaurants can be particularly difficult to clean in a dish machine due to the caramelized soil baked on to the surface of the ware. Some full-service restaurants have attempted to overcome this issue by using, as a pre-step to washing the pots and pans in the dish machine, a 3-compartment sink for soaking the pots and pans. Exemplary soaking solutions include water, pot and pan detergent solutions, or silverware presoaks. Components of these compositions typically include metal protectors, surfactants, alkalinity sources and the like. Surfactants are the single most important cleaning ingredient in cleaning products. The surfactants reduce the surface tension of water by adsorbing at the liquid-gas interface. They also reduce the interfacial tension between oil and water by adsorbing at the liquid-liquid interface. When dissolved in water, surfactants give a product the ability to remove soil from surfaces. Each surfactant molecule has a hydrophilic head that is attracted to water molecules and a hydrophobic tail that repels water and simultaneously attaches itself to oil and grease in soil. These opposing forces loosen the soil and suspend it in the water.

Surfactants do the basic work of detergents and cleaning compositions by breaking up stains and keeping the soil in the water solution to prevent re-deposition of the soil onto the surface from which it has just been removed. Surfactants disperse soil that normally does not dissolve in water. Environmental regulations, consumer habits, and consumer practices have forced new developments in the surfactant industry to produce lower-cost, higher-performing, and environmentally friendly products.

Antimicrobial agents are chemical compositions that are used to prevent microbiological contamination and deterioration of products, materials, and systems. Antimicrobial agents and compositions are used, for example, as disinfectants or sanitizers in association with hard surface cleaning, food preparation, hospitality services, hospital and medical uses, and hand soaps. There remains an ongoing need for antimicrobial compositions having the capability to be more concentrated while having foam stabilization for use compositions. Many cleaning compositions include a foaming agent to increase contact time on surfaces to be cleaned. Such compositions are presently used in many applications, such as retail, industrial and institutional including grease cutters, clinging lime scale removers, shower wall cleaners, bathtub cleaners, hand sanitizing gels, disinfectant gels, hand-soaps, teat dips, coatings, stabilized enzymes, structured liquids, and the like.

There remains a need highly active non-antimicrobial and antimicrobial compositions for various applications of use. However such formulations present challenges for foaming profiles and desired viscoelasticity less than about 900 cPS or preferably less than about 500 cPs, including compositions having an actives level of 30% or greater.

Accordingly, it is an objective of the claimed disclosure to develop concentrated and use liquid compositions and methods of using propoxylated compounds, including propoxylated surfactants and polymers, for various applications, including for example, soil removal applications to provide desired antimicrobial efficacy.

Still further, it is an object of the present disclosure to provide enhanced soil removal in non-antimicrobial applications employing propoxylated surfactants and polymers for foam stabilization in highly active compositions. In each aspect of the disclosure suitable foam stabilization is desired while providing safe, environmentally friendly and economically feasible compositions for various applications of use.

Other objects, advantages and features of the present invention will become apparent from the following specification taken in conjunction with the accompanying drawings.

BRIEF SUMMARY OF THE INVENTION

An advantage of the invention is the foam stabilization and enhancement in highly concentrated compositions of propoxylated compounds and anionic and/or nonionic surfactants, which can further include antimicrobial agents that maintain desired antimicrobial efficacy in the highly concentrated compositions. In additional embodiments non-antimicrobial compositions employ the combination of the propoxylated compounds and anionic and/or nonionic surfactants for soil removal with stabilized foam profiles. In an aspect, a concentrated antimicrobial or non-antimicrobial composition comprises: between about 1 wt-% and about 30 wt-% of a propoxylated EO/PO block copolymer surfactant (and/or propoxylated polymers); and between about 10 wt-% and about 90 wt-% of at least one anionic surfactant and/or nonionic surfactant; wherein the composition is a low viscoelasticity liquid concentrate having an active concentration of at least about 18% that is soluble in water and has a viscosity of less than about 900 cPs, has a pH of about 1 to about 12 in a use solution, and provides at least a 3 log microbial kill on a treated surface for the antimicrobial composition.

In a further embodiment, a kit to provide the concentrated antimicrobial or non-antimicrobial composition comprises: a two-part premix for a concentrated liquid composition comprising a first part and a second part; wherein the first part comprises a propoxylated EO/PO block copolymer surfactant (and/or propoxylated polymers); and wherein the second part comprises an anionic surfactant and solvent(s).

In a further embodiment, a method of cleaning a surface comprises: providing a liquid composition according to claim 1 to a surface; and optionally rinsing the surface in need thereof, wherein the composition provides commercially acceptable cleaning performance, and wherein the composition is effective at low and/or high temperatures.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
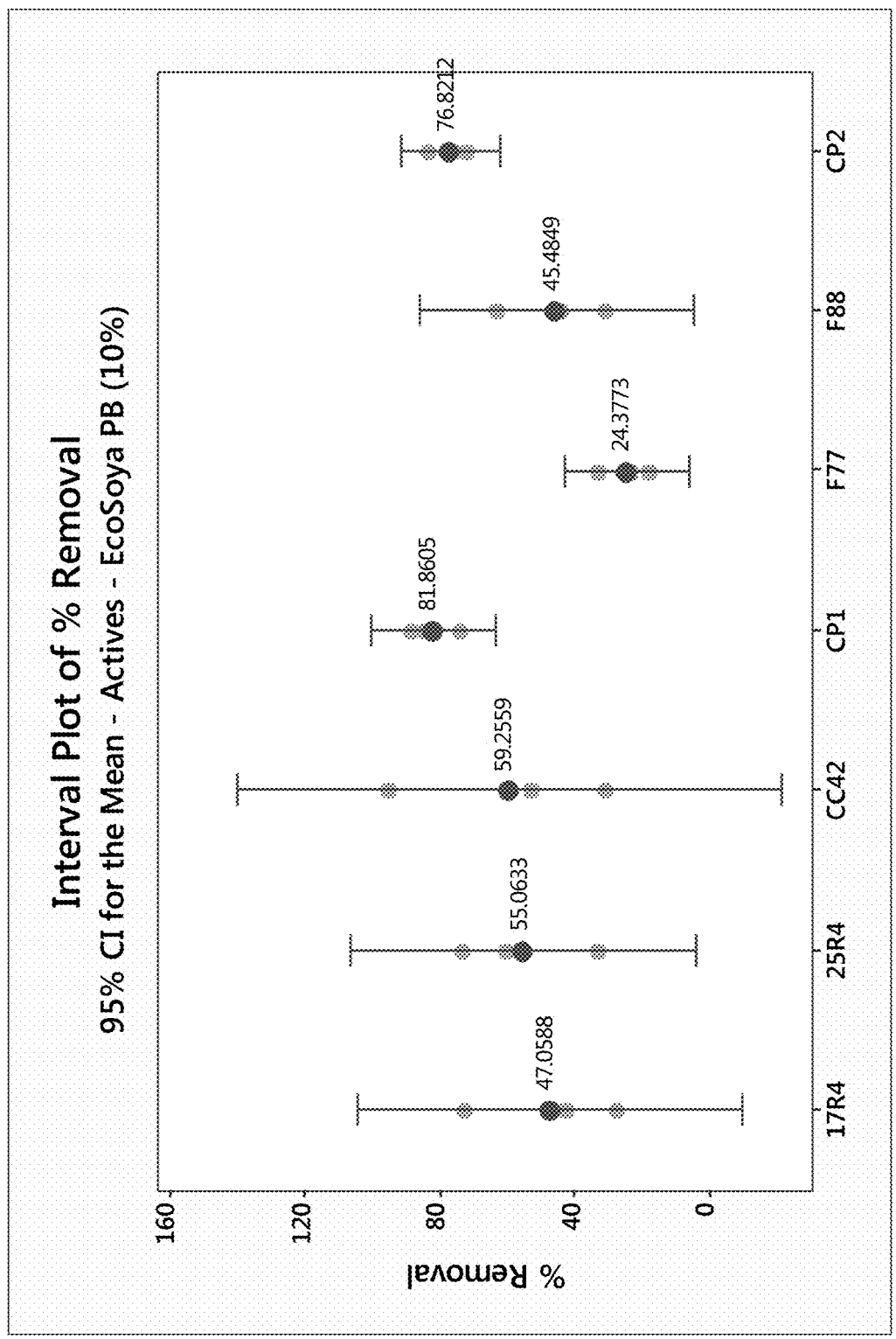
FIG. 1 shows an interval plot of the percentage of soil removal using various commercial controls (antimicrobial compositions) and compositions containing non-propoxylated surfactants compared to compositions containing propoxylated surfactants or polymers.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The embodiments of this invention are not limited to particular compositions, methods of making and/or methods of employing the same for cleaning, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

The term "commercially acceptable cleaning performance" refers generally to the degree of cleanliness, extent of effort, or both that a typical consumer would expect to achieve or expend when using a cleaning product or cleaning system to address a typical soiling condition on a typical substrate. This degree of cleanliness may, depending on the particular cleaning product and particular substrate, correspond to a general absence of visible soils, or to some lesser degree of cleanliness. For example, a shower cleaner or toilet bowl cleaner would be expected by a typical consumer to achieve an absence of visible soils when used on a moderately soiled but relatively new hard surface, but would not be expected to achieve an absence of visible soils when used on an old hard surface which already bears permanent stains such as heavy calcite deposits or iron discoloration. Cleanliness may be evaluated in a variety of ways depending on the particular cleaning product being used (e.g., ware or laundry detergent, rinse aid, hard surface cleaner, vehicular wash or rinse agent, or the like) and the particular hard or soft surface being cleaned (e.g., ware, laundry, fabrics, vehicles, and the like), and normally may be determined using generally agreed industry standard tests or localized variations of such tests. In the absence of such agreed industry standard tests, cleanliness may be evaluated using the test or tests already employed by a manufacturer or seller to evaluate the cleaning performance of its phosphorus-containing cleaning products sold in association with its brand.

For the purpose of this patent application, successful microbial reduction is achieved when the microbial populations are reduced by at least about 50%, or by significantly more than is achieved by a wash with water. Larger reductions in microbial population provide greater levels of protection.

An "extended chain surfactant" is a surfactant having an intermediate polarity linking chain, such as a block of poly-propylene oxide, or a block of poly-ethylene oxide, or a block of poly-butylene or a mixture thereof, inserted between the surfactant's conventional lipophilic segment and hydrophilic segment.

The term "hard surface" refers to a non-resilient cleanable substrate, for example materials made from ceramic, stone, glass or hard plastics including showers, sinks, toilets, bathtubs, countertops, windows, mirrors, transportation vehicles, walls, wooden or tile floors, patient-care equipment (for example diagnostic equipment, shunts, body scopes, wheel chairs, bed frames, etc.), surgical equipment and the like.

The term "improved cleaning performance" refers generally to achievement by a substitute cleaning product or substitute cleaning system of a generally greater degree of cleanliness or with generally a reduced expenditure of effort, or both, when using the substitute cleaning product or substitute cleaning system rather than a branded cleaning product to address a typical soiling condition on a typical substrate that does not employ the combination of the quaternary ammonium compound and anionic surfactant of the present disclosure. This degree of cleanliness may, depending on the particular cleaning product and particular substrate, correspond to a general absence of visible soils, or to some lesser degree of cleanliness, as explained above.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The term "surfactant" as used herein is a compound that contains a lipophilic segment and a hydrophilic segment, which when added to water or solvents, reduces the surface tension of the system.

The term "viscosity" or "viscoelasticity" as referred to herein is a measurement of the thickness of a fluid or how a fluid opposes the relative motion between two surfaces of the fluid that are moving at different velocities. Viscosity is a limiting factor for the ability to use conventional dispensers (e.g. aspirators) based on the relative thickness of the fluid, such as occurs in detergents formulated with high level of anionic surfactants. As referred to herein a viscosity of less than about 900 cPs is preferred to use conventional dispensors. As one skilled in the art appreciates, the viscosity of a fluid will vary depending upon the temperature of the fluid. In an embodiment, viscosity in cPs is measured at room temperature or at 40° F. (4° C.) (depending upon the application of use and dispensing of the fluid) and a desired viscosity for dispensing a fluid at either exemplary temperature is less than about 900 cPs.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Compositions

The compositions according to the disclosure include antimicrobial and non-antimicrobial compositions with enhanced foaming profiles with highly active concentrations, including at least 18% actives, from about 18-30% actives, from about 18-50% actives, at least 30% actives, or greater, while maintaining suitable viscoelasticity. In another aspect, the highly active compositions do not include viscoelastic reducing agents and/or provide a viscosity of less than about 900 cPs or less than about 500 cPs to enable use of conventional dispensers (e.g. aspirators). In a further aspect, the highly active compositions does not include viscoelastic reducing agents while still providing desired viscosity to enable use of conventional dispensers (e.g. aspirators). In an aspect, the compositions according to the disclosure comprise, consist of and/or consist essentially of a propoxylated EO/PO block copolymer surfactant (and/or propoxylated polymer) and high foaming surfactant(s), such as at least one anionic and/or nonionic surfactant. In an aspect, the compositions according to the disclosure comprise, consist of and/or consist essentially of a propoxylated surfactant or polymer and at least one surfactant providing a high viscoelasticity, such as at least one anionic and/or nonionic surfactant. In a still further aspect, the compositions according to the disclosure comprise, consist of and/or consist essentially of a propoxylated EO/PO block copolymer surfactant (and/or propoxylated polymer), at least one anionic surfactant, and at least one nonionic surfactant. In some preferred applications the inclusion of both the anionic surfactant with at least one nonionic surfactant provides further foam enhancement.

The compositions according to the disclosure overcome the insufficient surface activity of various propoxylated surfactants and polymers on its own and instead provide for highly concentrated actives in a formulation with the additional surfactants to provide efficacious antimicrobial capabilities with stabilized foam profiles. In various aspects, the compositions providing viscoelastic highly concentrated compositions ensure sufficient contact of the composition and soil removal for applications requiring stabilized foaming, including for example pot and pan cleaning and hand soaps. Beneficially, the selection of the propoxylated surfactant or polymer and the additional surfactants can provide such stabilized foaming within highly concentrated compositions, including at least 18% actives, from about 18-30% actives, at least 30% actives, 30-50% actives, or greater.

Nothing in the specification shall be also understood to limit the forming of a "super-concentrated" composition based upon the composition described above. A super-concentrated composition can beneficially provide actives greater than 30%, including between about 30% and about 50%, at least about 40%, or at least about 50%. As a result of such concentration any liquid compositions include a lesser amount of water. Beneficially, these concentrated compositions can be achieved without the use of any viscoelasticity reducing agents while still being capable of conventional commercial dispensing techniques (e.g. aspirators). Exemplary viscoelastic reducing agents which can be excluded from certain embodiments of the compositions, include for example ethanol, propylene glycol, glycerin, inorganic salts (e.g. sodium chloride) or the like.

The compositions provide the benefit of a significant viscosity (or viscoelasticity) reduction, resulting in ability of highly concentrated formulations according to the present disclosure. In an aspect, detergents formulated with high level of anionic surfactants can become viscous, however the combination according to the present disclosure overcomes any gelling concerns and provides ease of manufacturing and dispensing of the product from a container. Moreover, there are benefits in formulations such that diluted compositions (having a large amount of water in the formulation) are not shipped at great expense. Instead, the increased viscosity and therefore compactness of the compositions permit the transport of less weight, making shipping more economical; less packaging is required so that smaller and more readily disposable containers can be used; there is less chance for messy leakage; and less shelf space is required in the retail stores.

EMBODIMENTS

Exemplary ranges of the compositions according to the invention are shown in Table 1 each in weight percentage, and additional amounts of water can be added to formulations. Exemplary formulations employing the compositions according to the invention are shown in Tables 1A-1B and include, for example, hand soap compositions, soaking compositions, and pot and pan compositions.

TABLE 1A

| Material | First Exemplary Range wt-% | Second Exemplary Range wt-% | Third Exemplary Range wt-% |
|---|---|---|---|
| Propoxylated EO/PO Block Copolymer Surfactant (and/or Propoxylated Polymer) | 1-30 | 1-15 | 1-10 |
| At least one anionic surfactant and/or nonionic surfactant | 10-90 | 10-80 | 30-80 |
| Additional Functional Ingredients | 0-50 | 0.1-40 | 1-40 |
| Water or other Solvent(s) | Remainder if liquid | Remainder if liquid | Remainder if liquid |

TABLE 1B

| Material | First Exemplary Range wt-% | Second Exemplary Range wt-% | Third Exemplary Range wt-% |
|---|---|---|---|
| Propoxylated EO/PO Block Copolymer Surfactant (and/or Propoxylated Polymer) | 1-30 | 1-15 | 1-10 |
| At least one nonionic surfactant | 10-70 | 15-70 | 20-60 |
| At least one anionic surfactant | 1-40 | 5-30 | 10-30 |
| Additional Functional Ingredients | 0-50 | 0.1-40 | 1-40 |
| Water or other Solvent(s) | Remainder if liquid | Remainder if liquid | Remainder if liquid |

The antimicrobial compositions and non-antimicrobial compositions can be provided in single use or multiple use compositions. In a preferred aspect, the composition is a concentrated liquid or solid composition. Various solids can be employed according to the invention and without limiting the scope of the invention. It should be understood that compositions and methods embodying the invention are suitable for preparing a variety of solid compositions, as for example, a cast, extruded, pressed, molded or formed solid pellet, block, tablet, and the like. In some embodiments, the solid composition can be formed to have a weight of 50 grams or less, while in other embodiments, the solid composition can be formed to have a weight of 50 grams or greater, 500 grams or greater, or 1 kilogram or greater.

According to the disclosure, the compositions have a use pH from about 0 to about 12. In some aspects, the compositions of the invention have a pH between about 1 and about 12. In another embodiment the composition has a pH between about 4 and about 10. In another embodiment the composition has a pH between about 5 and about 9 and such compositions are particularly suitable for pot and pan applications where contact to skin is made. Without limiting the scope of invention, the numeric ranges are inclusive of the numbers defining the range and include each integer within the defined range. According to aspects of the invention, the diluted use solutions may have acidic or neutral to alkaline pH depending upon a particular application of use thereof and the desired non-corrosive nature of the applications.

Propoxylated Surfactant or Polymer

The compositions according to the invention include at least one propoxylated surfactant or polymer. In an aspect, the propoxylated surfactants or polymers can include EO/PO copolymers, PO polymers and copolymers, nonionic extended chain surfactants having a PO group, and anionic extended chain surfactants having a PO group, wherein the propoxylated compounds beneficially provides for low viscoelastic concentrate formulations as described herein. The use of propoxylated surfactants or polymers can replace, partially or wholly, traditional surfactants including anionic surfactants, present in foaming applications and provide a desired lowered viscosity thus allowing for easier manufacturing and dispensing. The lowered viscosity also allows for the development of super-concentrate formulations.

In a preferred aspect, the propoxylated surfactant is a propoxylated EO/PO block copolymer surfactant. The copolymer surfactants can include capped EO/PO copolymer surfactants. Exemplary EO/PO copolymers and capped EO/PO copolymers are alkoxylated surfactants suitable for use in the compositions. EO/PO block copolymers include commercially-available Pluronic® and reverse Pluronic® surfactants and are examples of polymeric compounds made from a sequential propoxylation and ethoxylation. EO/PO copolymers can be modified by "capping" or "end blocking" the terminal hydroxy group or groups (of multi-functional moieties).

In an aspect, the EO/PO block copolymer surfactants include (EO)n(PO)m(EO)n and (PO)m(EO)n(PO)m structures, wherein n and m are the average number of polymerized ethylene oxide and propylene oxide units, respectively, and can be calculated based on the percentage of EO/PO and molecular weight of a structures. In an aspect, the EO/PO block copolymer surfactants have a molecular weight of at least about 1000 g/mol, or at least about 2000 g/mol, or at least about 3000 g/mol, or at least about 4000 g/mol, or at least about 5000 g/mol, or at least about 6000 g/mol, or at least about 7000 g/mol, or at least about 8000 g/mol, or at least about 9000 g/mol, or at least about 10,000 g/mol, or at least about 11,000 g/mol, or at least about 12,000 g/mol, or at least about 13,000 g/mol, or at least about 14,000 g/mol, or at least about 15,000 g/mol.

In an aspect, the EO/PO block copolymer surfactants and capped EO/PO block copolymer surfactants have at least about 20% PO, at least about 30% PO, at least about 40% PO, at least about 50% PO, at least about 60% PO, at least about 70% PO, at least about 80% PO, or at least about 90% PO, and with a Ross Miles Foam of greater than or equal to 40 (0.1% @ 50° C.). Exemplary EO/PO block copolymers are commercially available under the tradename Pluronic®.

Block polyoxypropylene-polyoxyethylene polymeric compounds based upon propylene glycol, ethylene glycol, glycerol, trimethylolpropane, and ethylenediamine as the initiator reactive hydrogen compound. Pluronic® compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule. Tetronic® compounds are tetra-functional block copolymers derived from the sequential addition of propylene oxide and ethylene oxide to ethylenediamine. The molecular weight of the propylene oxide hydrotype ranges from about 500 to about 7,000; and, the hydrophile, ethylene oxide, is added to constitute from about 10% by weight to about 80% by weight of the molecule. Beneficially, Pluronic® compounds provide 100% actives. In an aspect, the propoxylated polymers can include PO polymers. PO polymers, PO-EO polymers and EO-PO polymers derived from polyethyleneimine (PEI) polymers, including PEI-PO, PEI-PO-EO, PEI-EO-PO and their salts or mixtures thereof. The PEI or PEIs are branched, spherical polymeric amines, and the molecular weight of the PEI or PEI salt used is from about 800 daltons to about 2 million Daltons. In addition, the charge density of the PEI or PEI salt used is from about 15 meq/g to about 25 meq/g, more preferably from about 16 meq/g to about 20 meq/g. Examples of such preferred PEIs include the BASF products LUPASOL WF (25 kDa; 16-20 meq/g) and Lupasol FG (800 daltons; 16-20 meq/g), and the SOKALAN family of polymers available from BASF.

In an aspect, the propoxylated surfactants can include one or more extended chain surfactants. These are surfactants that have, for example, an intermediate polarity poly-propylene oxide chain (or linker) inserted between the lipophilic tail group and hydrophilic polar head, which may be anionic or nonionic. Examples of lipophilic tails groups include hydrocarbons, alkyl ether, fluorocarbons or siloxanes. Examples of anionic and nonionic hydrophilic polar heads of the extended surfactant include, but are not necessarily limited to, groups such as polyoxyethylene sulfate, ethoxysulfate, carboxylate, ethoxy-carboxylate, C6 sugar, xylitol, di-xylitol, ethoxy-xylitol, carboxylate and xytol, carboxylate and glucose. In an aspect extended surfactants include a linker polypropylene glycol link.

Extended surfactants generally have the formula R-[L]x—[O—$CH_2$—$CH_2$]y where R is the lipophilic moiety, a linear or branched, saturated or unsaturated, substituted or unsubstituted, aliphatic or aromatic hydrocarbon radical having from about 8 to 20 carbon atoms, L is a linking group, such as a block of poly-propylene oxide, a block of poly-ethylene oxide, a block of poly-butylene oxide or a mixture thereof; x is the chain length of the linking group ranging from 5-25, or 5-15; and y is the average degree of ethoxylation ranging from 1-20, or 1-5.

Anionic extended surfactants generally have the formula R-[L]x—[O—$CH_2$—$CH_2$]y, or R-[L]x—[O—$CH_2$—$CH_2$]y M, where M is any ionic species such as carboxylates, sulfonates, sulfates, and phosphates and R is the lipophilic moiety, a linear or branched, saturated or unsaturated, substituted or unsubstituted, aliphatic or aromatic hydrocarbon radical having from about 8 to 20 carbon atoms, L is a linking group, such as a block of poly-propylene oxide, a block of poly-ethylene oxide, a block of poly-butylene oxide or a mixture thereof; x is the chain length of the linking group ranging from 5-15; and y is the average degree of ethoxylation ranging from 1-5. A cationic species will generally also be present for charge neutrality such as hydrogen, an alkali metal, alkaline earth metal, ammonium and ammonium ions which may be substituted with one or more organic groups. These extended chain surfactants attain low interfacial tension and/or high solubilization in a single phase microemulsion with oils, such as nontrans fats with additional beneficial properties including, but not necessarily limited to, insensitivity to temperature and irreversibility. For example, in one embodiment the emulsions may function over a relatively wide temperature range of from about 20 C to about 280 C, alternatively from about 20 C to about 180 C (350 F).

In a preferred embodiment the extended chain surfactant is an anionic extended chain surfactant with at least 5 moles of propoxylation. Most preferred is from about 5 to about 8 moles of propoxylation.

Nonionic extended surfactants having a PO extension include the formula R-[L]$_x$—O—CH$_2$—CH$_2$]$_y$ where R is the lipophilic moiety, such as a linear or branched, saturated or unsaturated, substituted or unsubstituted, aliphatic or aromatic hydrocarbon radical having from about 8 to 20 carbon atoms, L is a linking group, such as a block of poly-alkylene oxide, preferably polypropylene oxide; x is the chain length of the linking group ranging from 2-25; and y is the average degree of ethoxylation ranging from 1-18. In a preferred embodiment, the extended chain nonionic surfactant has enough PO extension as the main surfactant (and only) can form liquid single phase microemulsions. PO length is optimized at from about 5 to about 8 moles of PO. This length of PO extension provides a lower foam profile. Moreover, R groups that are a branched hydrophobe such as a guerbet alcohol are better for protein soil defoaming.

In an aspect, preferred nonionic extended surfactants include: branched Guerbet alcohol alkoxylates; such as $C_{10}(PO)_8(EO)_x$ (x=3,6,8,10) also, extended linear alcohol alkoxylates; $C_{(12-14)}(PO)_{16}(EO)_x$ (x=6,12,17). Preferred branched alcohol alkoxylates include Guerbet ethoxylates. Guerbet ethoxylates suitable for use according to the invention have the following formula:

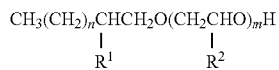

In an aspect the Guerbet ethoxylate is further defined wherein R1 is C2-C20 alkyl and R2 is H or C1-C4 alkyl. In a further aspect, the Guerbet ethoxylate is defined wherein "n" is an integer between 2 and 20 and wherein "m" is an integer between 1 and 40. In a preferred aspect, the branched alcohol alkoxylate is a Guerbet ethoxylate that is prepared from a Guerbet alcohol by dimerization of alkenes (e.g. butane). The branched alcohol alkoxylates, including Guerbet ethoxylates, can be prepared according to U.S. Pat. Nos. 6,906,320, 6,737,553 and 5,977,048, the disclosure of these patents are herein incorporated by reference in their entirety. Exemplary branched alcohol alkoxylates include those available under the tradenames Lutensol XP-30 and Lutensol XP-50 (BASF Corporation). In general, Lutensol XP-30 can be considered to have 3 repeating ethoxy groups, and Lutensol XP-50 can be considered to have 5 repeating ethoxy groups. Branched alcohol alkoxylates can be classified as relatively water insoluble or relatively water soluble. In general, a water insoluble branched alcohol alkoxylate can be considered an alkoxylate that, when provided as a composition containing 5 wt.-% of the branched alcohol alkoxylate and 95 wt.-% water, has a tendency to phase separate. Lutensol XP-30 and Lutensol XP-50 from BASF Corporation are examples of water-insoluble branched alcohol alkoxylates.

Capped extended nonionic surfactants are also suitable for use to lower the foam profile of the composition and foam from protein soil. Capped extended nonionic surfactants can include: R-[PO]$_x$-[EO]$_y$[N]z, where N is a capping group such as an alkyl group such as methyl, benzyl, butyl, etc.; a PO group of from 1-5 length, in length. These extended chain surfactants attain low tension and/or high solubilization, and can from a single phase microemulsion with oils, such as non-trans fats with additional beneficial properties including, but not necessarily limited to, tunability to temperature and irreversibility within the microemulsion forming temperature range. For example, in one embodiment the emulsions or microemulsions may function over a relatively wide temperature range of from about 80° to 190° C. For example with a PO length of 8, and R as a Guerbet alcohol, extended nonionic surfactants tested according to the invention formed stable microemulsions for 3E0 at 90°-80°; 6 EO at 160°-120°; 8EO 150°-185° and 10 EO 165°-190°. Thus one can customize the extended nonionic surfactant for the type of cleaning system used, and at what temperature one wants the micro emulsion to form.

An effective amount of the propoxylated surfactant or polymer is provided in combination with the at least one anionic surfactant and/or nonionic surfactant. Suitable concentrations of the propoxylated surfactant or polymer in concentrate compositions include between about 1 wt-% to about 50 wt-%, about 1 wt-% to about 30 wt-%, about 1 wt-% to about 25 wt-%, about 1 wt-% to about 20 wt-%, about 5 wt-% to about 30 wt-%, about 5 wt-% to about 25 wt-%, about 5-wt-% to about 20 wt-%, about 5 wt-% to about 15 wt-%, or about 5 wt-% to about 10 wt-%. Without being limited according to the invention, all ranges recited are inclusive of the numbers defining the range and include each integer within the defined range.

High Concentration Surfactants and/or High Foaming Surfactants and/or Viscoelastic Compositions The compositions according to the disclosure include at least one high foaming surfactant, such as at least one anionic and/or nonionic surfactant. In another aspect, the compositions according to the disclosure include at least one surfactant at a high concentration, such as would form a gel, or those providing a high viscoelasticity in water, such as at least one anionic and/or nonionic surfactant. Various combinations of such surfactants can be included at high actives while beneficially retaining desired viscoelasticity of the compositions. In an exemplary embodiment, the compositions include an anionic surfactant and at least two nonionic surfactants. In a further exemplary embodiment, the compositions include an anionic surfactant and a nonionic surfactant.

Anionic Surfactants

The compositions according to the disclosure include at least one anionic surfactant and/or nonionic surfactant. In other aspects, the compositions according to the invention include at least two anionic surfactants. Anionic surfactants are categorized as anionics because the charge on the hydrophobe is negative; or surfactants in which the hydrophobic section of the molecule carries no charge unless the pH is elevated to neutrality or above (e.g. carboxylic acids). Carboxylate, sulfonate, sulfate and phosphate are polar (hydrophilic) solubilizing groups found in anionic surfactants.

As those skilled in the art understand, anionics are excellent detersive surfactants and are therefore traditionally favored additions to heavy duty detergent compositions. Generally, anionics have high foam profiles which are useful for the present foaming cleaning compositions. Anionic surface active compounds are useful to impart special chemical or physical properties other than detergency within the composition.

The majority of large volume commercial anionic surfactants can be subdivided into major chemical classes and additional sub-groups known to those of skill in the art and described in "Surfactant Encyclopedia," Cosmetics & Toiletries, Vol. 104 (2) 71-86 (1989). The first class includes acylamino acids (and salts), such as acylgluamates, acyl peptides, sarcosinates (e.g. N-acyl sarcosinates), taurates (e.g. N-acyl taurates and fatty acid amides of methyl tauride), and the like. The second class includes carboxylic acids (and salts), such as alkanoic acids (and alkanoates), ester carboxylic acids (e.g. alkyl succinates), ether carboxylic acids, and the like. The third class includes sulfonic acids (and salts), such as isethionates (e.g. acyl isethionates), alkylaryl sulfonates, alkyl sulfonates, sulfosuccinates (e.g. monoesters and diesters of sulfosuccinate), and the like. The fourth class includes sulfuric acid esters (and salts), such as alkyl ether sulfates, alkyl sulfates, and the like. A particularly preferred anionic surfactant is sodium laurel ether sulfate.

In an aspect, the anionic surfactant is linear or branched. In an aspect, the linear or branched anionic surfactant is a medium chain surfactant having from 6-18 carbon chain length, preferably from 6-12 carbon chain length, and more preferably from 6-10 carbon chain length. In an aspect, the linear or branched, medium chain anionic surfactant is alkoxylated. In an aspect, the linear or branched anionic surfactant is an alkoxylated medium chain surfactant having from 6-18 carbon chain length, preferably from 6-13 carbon chain length, and more preferably from 6-10 carbon. In an aspect, the anionic surfactant is a carboxylate. In an alternative aspect, the anionic surfactant is a weak acid anionic, such as a phosphate ester. In a still further alternative aspect, the anionic surfactant is a sulfonate and/or sulfate.

In an aspect, the anionic surfactants suitable for use in the present compositions include carboxylates. Anionic carboxylate surfactants suitable for use in the present compositions include carboxylic acids (and salts), such as alkanoic acids (and alkanoates), ester carboxylic acids (e.g. alkyl succinates), ether carboxylic acids, sulfonated fatty acids, such as sulfonated oleic acid, and the like Suitable carboxylic acids include for example decanoic acid, octanoic acid, nonanoic, ethylhexyl acid, and isononanionic acid. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula: R—O—(CH$_2$CH$_2$O)$_n$(CH$_2$)$_m$—CO$_2$X in which R is a C8-C22 alkyl group or

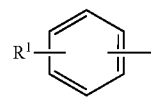

in which R$^1$ is a C4-C16 alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a C8-C16 alkyl group. In some embodiments, R is a C12-C14 alkyl group, n is 4, and m is 1.

Such alkyl and alkylaryl ethoxy carboxylates are commercially available. These ethoxy carboxylates are typically available as the acid forms, which can be readily converted to the anionic or salt form.

In an aspect, the anionic surfactants suitable for use in the present compositions include phosphate esters.

In an aspect, the anionic surfactants suitable for use in the present compositions include sulfonates and/or sulfates. In an aspect, the anionic surfactant suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the C5-C17 acyl-N—(C1-C4 alkyl) and —N—(C1-C2 hydroxyalkyl) glucamine sulfates, and sulfates of alkylpolysaccharides such as the sulfates of alkylpolyglucoside, and the like. Also included are the alkyl sulfates, alkyl poly (ethyleneoxy) ether sulfates and aromatic poly(ethyleneoxy) sulfates such as the sulfates or condensation products of ethylene oxide and nonyl phenol (usually having 1 to 6 oxyethylene groups per molecule). Anionic sulfonate surfactants suitable for use in the present compositions also include alkyl sulfonates, the linear and branched primary and secondary alkyl sulfonates, and the aromatic sulfonates with or without substituents.

Examples of anionic carboxylate surfactants suitable for use in the compositions include organic acids such as hexanoic acid, heptanoic acid, octanoic acid, nonanoic acid, and decanoic acid. Examples of branched chain organic acids suitable for use in the 2-in-1 sanitizing rinse compositions include ethylhexyl carboxylate, isononanoic carboxylate, and tridecyl carboxylate. Examples of commercially available surfactants suitable for use in the 2-in-1 sanitizing rinse compositions include organic acids such as hexanoic acid, heptanoic acid, octanoic acid, nonanoic acid, decanoic acid, Colatrope INC, Isononanionic acid, Marlowet 4539 (C9-alcohol polyethylene glycol ether carboxylic acid available from Sasol), Emulsogen CNO (C8-alcohol 8 moles polyethylene glycol ether carboxylic acid available from Clariant), and Emulsogen DTC (C13-alcohol 7 moles polyethylene glycol ether carboxylic acid available from Clariant).

An effective amount of the anionic surfactant includes between about 1 wt-% to about 50 wt-%, about 1 wt-% to about 45 wt-%, about 1 wt-% to about 40 wt-%, about 1 wt-% to about 35 wt-%, about 1 wt-% to about 30 wt-%, about 5 wt-% to about 40 wt-%, about 5 wt-% to about 30 wt-%, about 10 wt-% to about 30 wt-%, or about 10 wt-% to about 25 wt-%. Without being limited according to the invention, all ranges recited are inclusive of the numbers defining the range and include each integer within the defined range.

Nonionic Surfactants

In some aspects, the compositions according to the disclosure include at least one nonionic surfactant. In other aspects, the compositions according to the invention include at least two nonionic surfactants. Useful nonionic surfactants are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties. Useful nonionic surfactants include:

Suitable nonionic surfactants suitable for use with the compositions include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants include EO/PO block copolymers, such as the Pluronic® and reverse Pluronic® surfactants; alcohol alkoxylates, such as Dehypon® LS-54 (R-(EO)$_5$(PO)$_4$) and Dehypon® LS-36 (R-(EO)$_3$(PO)$_6$); and capped alcohol alkoxylates, such as Plurafac® LF221 and Tegoten® EC11; mixtures thereof, or the like.

Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available under the trade names Pluronic® and Tetronic® manufactured by BASF Corp. Pluronic® compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule. Tetronic® compounds are tetra-functional block copolymers derived from the sequential addition of propylene oxide and ethylene oxide to ethylenediamine. The molecular weight of the propylene oxide hydrotype ranges from about 500 to about 7,000; and, the hydrophile, ethylene oxide, is added to constitute from about 10% by weight to about 80% by weight of the molecule.

Condensation products of one mole of alkyl phenol wherein the alkyl chain, of straight chain or branched chain configuration, or of single or dual alkyl constituent, contains from about 8 to about 18 carbon atoms with from about 3 to about 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal® manufactured by Rhodia and Triton® manufactured by Dow Chemical Company.

Condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Neodol® manufactured by Shell Chemical Co. and Alfonic® manufactured by Sasol North America Inc.

Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above defined carbon atoms range or it can consist of an acid having a specific number of carbon atoms within the range.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention for specialized embodiments, particularly indirect food additive applications. All of these ester moieties have one or more reactive hydrogen sites on their molecule which can undergo further acylation or ethylene oxide (alkoxide) addition to control the hydrophilicity of these substances. Care must be exercised when adding these fatty ester or acylated carbohydrates to compositions of the present invention containing amylase and/or lipase enzymes because of potential incompatibility.

Examples of nonionic low foaming surfactants include:

The alkylphenoxypolyethoxyalkanols of U.S. Pat. No. 2,903,486 issued Sep. 8, 1959 to Brown et al. and represented by the formula

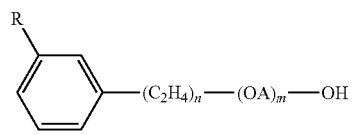

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula Z[(OR)$_n$OH]$_z$ wherein Z is alkoxylatable material, R is a radical derived from an alkaline oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula Y(C$_3$H$_6$O)n (C$_2$H$_4$O)$_m$H$_x$ wherein Y is the residue of organic compound having from about 1 to 6 carbon atoms and one reactive hydrogen atom, n has an average value of at least about 6.4, as determined by hydroxyl number and m has a value such that the oxyethylene portion constitutes about 10% to about 90% by weight of the molecule.

The conjugated polyoxyalkylene compounds described in U.S. Pat. No. 2,674,619, issued Apr. 6, 1954 to Lundsted et al. having the formula $Y[(C_3H_6O)_n (C_2H_4O)_mH]_x$ wherein Y is the residue of an organic compound having from about 2 to 6 carbon atoms and containing x reactive hydrogen atoms in which x has a value of at least about 2, n has a value such that the molecular weight of the polyoxypropylene hydrophobic base is at least about 900 and m has value such that the oxyethylene content of the molecule is from about 10% to about 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this invention correspond to the formula: $P[(C_3H_6O)_n (C_2H_4O)_mH]_x$ wherein P is the residue of an organic compound having from about 8 to 18 carbon atoms and containing x reactive hydrogen atoms in which x has a value of 1 or 2, n has a value such that the molecular weight of the polyoxyethylene portion is at least about 44 and m has a value such that the oxypropylene content of the molecule is from about 10% to about 90% by weight. In either case the oxypropylene chains may contain optionally, but advantageously, small amounts of ethylene oxide and the oxyethylene chains may contain also optionally, but advantageously, small amounts of propylene oxide.

Polyhydroxy fatty acid amide surfactants suitable for use in the present compositions include those having the structural formula $R_2CON_{R1}Z$ in which: R1 is H, $C_1$-$C_4$ hydrocarbyl, 2-hydroxy ethyl, 2-hydroxy propyl, ethoxy, propoxy group, or a mixture thereof; $R_2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

The alkyl ethoxylate condensation products of aliphatic alcohols with from about 0 to about 25 moles of ethylene oxide are suitable for use in the present compositions. The alkyl chain of the aliphatic alcohol can either be straight or branched, primary or secondary, and generally contains from 6 to 22 carbon atoms.

The ethoxylated $C_6$-$C_{18}$ fatty alcohols and $C_6$-$C_{18}$ mixed ethoxylated and propoxylated fatty alcohols are suitable surfactants for use in the present compositions, particularly those that are water soluble. Suitable ethoxylated fatty alcohols include the C6-C18 ethoxylated fatty alcohols with a degree of ethoxylation of from 3 to 50.

Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

A further class of nonionic surfactants, which can be used as ingredients of the composition of the first component according to the invention, is that of the alkyl polyglycosides (APG). Suitable alkyl polyglycosides satisfy the general Formula RO(G)z where R is a linear or branched, particularly 2-methyl-branched, saturated or unsaturated aliphatic radical containing 8 to 22 and preferably 12 to 18 carbon atoms and G stands for a glycose unit containing 5 or 6 carbon atoms, preferably glucose. The degree of oligomerization z is a number between about 1.0 and about 4.0 and preferably between about 1.1 and about 1.8.

Fatty acid amide surfactants suitable for use the present compositions include those having the formula: $R_6CON(R_7)_2$ in which R6 is an alkyl group containing from 7 to 21 carbon atoms and each R7 is independently hydrogen, $C_1$-$C_4$ alkyl, $C_1$-$C_4$ hydroxyalkyl, or $-(C_2H_4O)xH$, where x is in the range of from 1 to 3.

The treatise *Nonionic Surfactants*, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and detergents" (Vol. I and II by Schwartz, Perry and Berch). Additional disclosure of suitable nonionic surfactants for employing in combination with the anionic surfactant and quaternary ammonium compounds according to the invention are disclosed in U.S. Pat. No. 9,309,485, the entire contents of which are herein incorporated by reference in its entirety.

Semi-Polar Nonionic Surfactants

The semi-polar type of nonionic surface active agents are another class of nonionic surfactant useful in compositions. Generally, semi-polar nonionics are high foamers and foam stabilizers. However, within compositional embodiments designed for high foam cleaning methodology, semi-polar nonionics would have immediate utility. The semi-polar nonionic surfactants include the amine oxides, phosphine oxides, sulfoxides and their alkoxylated derivatives.

Amine oxides are tertiary amine oxides corresponding to the general formula:

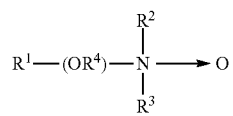

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure;

$R^4$ is an alkaline or a hydroxyalkylene group containing 2 to 3 carbon atoms; and n ranges from 0 to about 20.

Useful water soluble amine oxide surfactants are selected from the coconut or tallow alkyl di-(lower alkyl) amine oxides, specific examples of which are dodecyldimethylamine oxide, tridecyldimethylamine oxide, etradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water soluble phosphine oxides having the following structure:

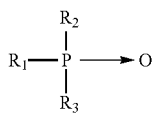

wherein the arrow is a conventional representation of a semi-polar bond; and, $R^1$ is an alkyl, alkenyl or hydroxyalkyl moiety ranging from 10 to about 24 carbon atoms in chain length; and, $R^2$ and $R^3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphone oxide, dimethylhexadecylphosphine oxide, diethyl-2-hydroxyoctyldecylphosphine oxide, bis(2-hydroxyethyl)dodecylphosphine oxide, and bis(hydroxymethyl)tetradecylphosphine oxide.

Semi-polar nonionic surfactants useful herein also include the water soluble sulfoxide compounds which have the structure:

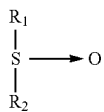

wherein the arrow is a conventional representation of a semi-polar bond; and, $R^1$ is an alkyl or hydroxyalkyl moiety of about 8 to about 28 carbon atoms, from 0 to about 5 ether linkages and from 0 to about 2 hydroxyl substituents; and $R^2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

Semi-polar nonionic surfactants for the compositions include dimethyl amine oxides, such as lauryl dimethyl amine oxide, myristyl dimethyl amine oxide, cetyl dimethyl amine oxide, combinations thereof, and the like. Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

An effective amount of the nonionic surfactant is provided including between about 1 wt-% to about 70 wt-%, about 10 wt-% to about 70 wt-%, about 15 wt-% to about 70 wt-%, about 15 wt-% to about 60 wt-%, about 20 wt-% to about 60 wt-%, or about 25 wt-% to about 60 wt. Without being limited according to the invention, all ranges recited are inclusive of the numbers defining the range and include each integer within the defined range.

Additional Functional Ingredients

The components of the compositions can further be combined with various functional components. In some embodiments, the compositions including the propoxylated surfactant and/or polymer and anionic and/or nonionic surfactants make up a large amount, or even substantially all of the total weight of the composition. For example, in some embodiments few or no additional functional ingredients are disposed therein. In other embodiments, additional functional ingredients may be included in the compositions. The functional ingredients provide desired properties and functionalities to the compositions. For the purpose of this application, the term "functional ingredient" includes a material that when dispersed or dissolved in the aqueous use solution provides a beneficial property in a particular use. Some particular examples of functional materials are discussed in more detail below, although the particular materials discussed are given by way of example only, and that a broad variety of other functional ingredients may be used.

In some embodiments, the compositions may include additional functional ingredients including, for example, additional surfactants, thickeners and/or viscosity modifiers, solvents, solubility modifiers, humectants, metal protecting agents, stabilizing agents, corrosion inhibitors, additional sequestrants and/or chelating agents, oxidizing agents, solidifying agent, sheeting agents, pH modifying components, including alkalinity and/or acidity sources, aesthetic enhancing agents (i.e., colorants, odorants, or perfumes), preservative, other cleaning agents, hydrotropes or couplers, buffers, and the like.

In some embodiments, the compositions do not include additional functional ingredients. In certain embodiments, the compositions do not include cationic surfactants. In certain embodiments, the compositions do not include viscoelasticity modifiers (or solubility modifiers or the like), including for example ethanol, propylene glycol, glycerin, inorganic salts (e.g. sodium chloride) or the like. In other embodiments, compositions may include viscoelasticity modifies having low VOC and do not have a low flash point.

Water

Water can be included in the concentrated liquid compositions. In some aspects, between about 10 wt-% and about 75 wt-%, between about 20 wt-% and about 60 wt-%, or between about 30 wt-% and about 60 wt-% water are in the concentrated liquid compositions.

Solvents

In an optional embodiment, one or more solvents can be included in the concentrated liquid compositions. In an aspect at least two solvents are included in the concentrated liquid compositions. Exemplary solvents include lower alkanols, lower alkyl ethers, and lower alkyl glycol ethers. Examples of such useful solvents include methanol, ethanol, propanol, isopropanol and butanol, isobutanol, ethylene glycol, diethylene glycol, triethylene glycol, propylene glycol, hexylene glycol, dipropylene glycol, mixed ethylene-propylene glycol ethers. The glycol ethers include lower alkyl (C1-8 alkyl) ethers including propylene glycol methyl ether, propylene glycol ethyl ether, propylene glycol propyl ether, dipropylene glycol methyl ether, dipropylene glycol ethyl ether, tripropylene glycol methyl ether, ethylene glycol methyl ether, ethylene glycol ethyl ether, ethylene glycol butyl ether, diethylene glycol methyl ether, diethylene glycol butyl ether, ethylene glycol dimethyl ether, ethylene glycol monobutyl ether, and others.

Certain embodiments may benefit from the inclusion of solvents in the formulation, such as for example propylene glycol and/or hexylene glycol. In the event a solvent is employed to assist with the viscoelasticity of the highly concentrated liquid composition, a solvent with low VOC is preferred. In the event a solvent is employed, it is further desired to employ a solvent with a high flash point (e.g. propylene glycol and/or hexylene glycol). In a preferred embodiment, a branched structure of a solvent is preferred, such as propylene glycol and/or hexylene glycol.

In some aspects, between about 1 wt-% and about 30 wt-%, between about 1 wt-% and about 20 wt-%, or between about 5 wt-% and about 15 wt-% solvent(s) are in the concentrated liquid compositions.

Alkalinity and/or Acidity Source

In some embodiments, the compositions can include a pH modifier to increase (e.g. strong acid or weak acid) or decrease (e.g. strong base or weak base) the pH of the compositions.

Stabilizing Agents

In some embodiments, the compositions of the present invention include dipicolinic acid as a stabilizing agent. Compositions including dipicolinic acid can be formulated to be free or substantially free of phosphorous. It has also been observed that the inclusion of dipicolinic acid in a composition of the present invention aids in achieving the phase stability of the compositions, compared to other conventional stabilizing agents, e.g., 1-hydroxy ethylidene-1,1-diphosphonic acid ($CH_3C(PO_3H_2)_2OH$) (HEDP). Additional suitable stabilizing agents include, for example, chelating agents or sequestrants.

In certain embodiments, the present composition includes about 0 wt-% to about 50 wt-% stabilizing agent, about 0 wt-% to about 20 wt-% stabilizing agent, about 0 wt-% to about 10 wt-% stabilizing agent, about 0.01 wt-% to about 10 wt-% stabilizing agent, about 0.4 wt-% to about 4 wt-% stabilizing agent, about 0.6 wt-% to about 3 wt-% stabilizing agent, about 1 wt-% to about 2 wt-% stabilizing agent. It is to be understood that all values and ranges within these values and ranges are encompassed by the present invention.

Sequestrants

The composition can contain an organic or inorganic sequestrant or mixtures of sequestrants. Organic sequestrants such as sodium citrate, the alkali metal salts of nitrilotriacetic acid (NTA), dicarboxymethyl glutamic acid tetrasodium salt (GLDA), EDTA, alkali metal gluconates, polyelectrolytes such as a polyacrylic acid, and the like can be used herein. The most preferred sequestrants are organic sequestrants such as sodium gluconate due to the compatibility of the sequestrant with the formulation base.

Suitable sequestrants include, but are not limited to, organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, aminocarboxylic acids, or heterocyclic carboxylic acids, e.g., pyridine-2,6-dicarboxylic acid (dipicolinic acid).

In other embodiments, the sequestrant can be or include phosphonic acid or phosphonate salt. Suitable phosphonic acids and phosphonate salts include HEDP; ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; picolinic, dipicolinic acid or mixtures thereof. In some embodiments, organic phosphonates, e.g., HEDP are included in the compositions of the present invention. Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino(tri(methylenephosphonic acid)), ($N[CH_2PO_3H_2]_3$), available from Monsanto as DEQUEST® 2000; ethylenediamine[tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The sequestrant can be or include aminocarboxylic acid type sequestrant. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and Alanine-N,N-diacetic acid; and the like; and mixtures thereof.

The sequestrant can be or include a polycarboxylate. Suitable polycarboxylates include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

The present invention can also incorporate sequestrants to include materials such as, complex phosphate sequestrants, including sodium tripolyphosphate, sodium hexametaphosphate, and the like, as well as mixtures thereof. Phosphates, the sodium condensed phosphate hardness sequestering agent component functions as a water softener, a cleaner, and a detergent builder. Alkali metal (M) linear and cyclic condensed phosphates commonly have a $M_2O:P_2O_5$ mole ratio of about 1:1 to 2:1 and greater. Typical polyphosphates of this kind are the preferred sodium tripolyphosphate, sodium hexametaphosphate, sodium metaphosphate as well as corresponding potassium salts of these phosphates and mixtures thereof. The particle size of the phosphate is not critical, and any finely divided or granular commercially available product can be employed.

Metal Protectors

The compositions of the invention can contain a material that can protect metal from corrosion. Such metal protectors include for example sodium gluconate and sodium glucoheptonate. If present, the metal protector is present in the composition in an amount of from about 0.1 wt-% to about 10 wt-%.

Solidification Agents

If it is desirous to prepare compositions of the invention as a solid, a solidification agent may be included into the composition. In some embodiments, the solidification agent can form and/or maintain the composition as a solid. In other embodiments, the solidification agent can solidify the composition without unacceptably detracting from the eventual release of the active ingredients. The solidification agent can include, for example, an organic or inorganic solid compound having a neutral inert character or making a functional, stabilizing or detersive contribution to the present composition. Suitable solidification agents include solid polyethylene glycol (PEG), solid polypropylene glycol, solid EO/PO block copolymer, amide, urea (also known as carbamide), nonionic surfactant (which can be employed with a coupler), anionic surfactant, starch that has been made water-soluble (e.g., through an acid or alkaline treatment process), cellulose that has been made water-soluble, inorganic agent, poly(maleic anhydride/methyl vinyl ether), polymethacrylic acid, other generally functional or inert materials with high melting points, mixtures thereof, and the like;

Suitable glycol solidification agents include a solid polyethylene glycol or a solid polypropylene glycol, which can, for example, have molecular weight of about 1,400 to about 30,000. In certain embodiments, the solidification agent includes or is solid PEG, for example PEG 1500 up to PEG 20,000. In certain embodiments, the PEG includes PEG 1450, PEG 3350, PEG 4500, PEG 8000, PEG 20,000, and the like. Suitable solid polyethylene glycols are commercially available from Union Carbide under the tradename CARBOWAX.

Suitable amide solidification agents include stearic monoethanolamide, lauric diethanolamide, stearic diethanolamide, stearic monoethanol amide, cocodiethylene amide, an alkylamide, mixtures thereof, and the like. In an embodiment, the present composition can include glycol (e.g., PEG) and amide.

Suitable nonionic surfactant solidification agents include nonylphenol ethoxylate, linear alkyl alcohol ethoxylate, ethylene oxide/propylene oxide block copolymer, mixtures thereof, or the like. Suitable ethylene oxide/propylene oxide block copolymers include those sold under the Pluronic tradename (e.g., Pluronic 108 and Pluronic F68) and commercially available from BASF Corporation. In some embodiments, the nonionic surfactant can be selected to be solid at room temperature or the temperature at which the composition will be stored or used. In other embodiments, the nonionic surfactant can be selected to have reduced aqueous solubility in combination with the coupling agent. Suitable couplers that can be employed with the nonionic surfactant solidification agent include propylene glycol, polyethylene glycol, mixtures thereof, or the like.

Suitable anionic surfactant solidification agents include linear alkyl benzene sulfonate, alcohol sulfate, alcohol ether sulfate, alpha olefin sulfonate, mixtures thereof, and the like. In an embodiment, the anionic surfactant solidification agent is or includes linear alkyl benzene sulfonate. In an embodiment, the anionic surfactant can be selected to be solid at room temperature or the temperature at which the composition will be stored or used.

Suitable inorganic solidification agents include phosphate salt (e.g., alkali metal phosphate), sulfate salt (e.g., magnesium sulfate, sodium sulfate or sodium bisulfate), acetate salt (e.g., anhydrous sodium acetate), Borates (e.g., sodium borate), Silicates (e.g., the precipitated or fumed forms (e.g., Sipernat 50® available from Degussa), carbonate salt (e.g., calcium carbonate or carbonate hydrate), other known hydratable compounds, mixtures thereof, and the like. In an embodiment, the inorganic solidification agent can include organic phosphonate compound and carbonate salt, such as an E-Form composition.

In some embodiments, the compositions of the present invention can include any agent or combination of agents that provide a requisite degree of solidification and aqueous solubility can be included in the present compositions. In other embodiments, increasing the concentration of the solidification agent in the present composition can tend to increase the hardness of the composition. In yet other embodiments, decreasing the concentration of solidification agent can tend to loosen or soften the concentrate composition.

In some embodiments, the solidification agent can include any organic or inorganic compound that imparts a solid character to and/or controls the soluble character of the present composition, for example, when placed in an aqueous environment. For example, a solidifying agent can provide controlled dispensing if it has greater aqueous solubility compared to other ingredients in the composition. Urea can be one such solidification agent. By way of further example, for systems that can benefit from less aqueous solubility or a slower rate of dissolution, an organic nonionic or amide hardening agent may be appropriate.

In some embodiments, the compositions of the present invention can include a solidification agent that provides for convenient processing or manufacture of the present composition. For example, the solidification agent can be selected to form a composition that can harden to a solid form under ambient temperatures of about 30 to about 50° C. after mixing ceases and the mixture is dispensed from the mixing system, within about 1 minute to about 3 hours, or about 2 minutes to about 2 hours, or about 5 minutes to about 1 hour.

The compositions of the present invention can include solidification agent at any effective amount. The amount of solidification agent included in the present composition can vary according to the type of composition, the ingredients of the composition, the intended use of the composition, the quantity of dispensing solution applied to the solid composition over time during use, the temperature of the dispensing solution, the hardness of the dispensing solution, the physical size of the solid composition, the concentration of the other ingredients, the concentration of the cleaning agent in the composition, and other like factors. Suitable amounts can include about 1 wt-% to about 99 wt-%, about 1.5 wt-% to about 85 wt-%, about 2 wt-% to about 80 wt-%, about 10 wt-% to about 45 wt-%, about 15 wt-% to about 40 wt-%, about 20 wt-% to about 30 wt-%, about 30 wt-% to about 70 wt-%, about 40 wt-% to about 60 wt-%, up to about 50 wt-%, about 40 wt-% to about 50 wt-%.

Dyes/Odorants

Various dyes, odorants including perfumes, and other aesthetic enhancing agents may also be included in the compositions. Examples of suitable commercially available dyes include, but are not limited to: Direct Blue 86, available from Mac Dye-Chem Industries, Ahmedabad, India; Fastusol Blue, available from Mobay Chemical Corporation, Pittsburgh, Pa.; Acid Orange 7, available from American Cyanamid Company, Wayne, N.J.; Basic Violet 10 and Sandolan Blue/Acid Blue 182, available from Sandoz, Princeton, N.J.; Acid Yellow 23, available from Chemos GmbH, Regenstauf, Germany; Acid Yellow 17, available from Sigma Chemical, St. Louis, Mo.; Sap Green and Metanil Yellow, available from Keystone Aniline and Chemical, Chicago, Ill.; Acid Blue 9, available from Emerald Hilton Davis, LLC, Cincinnati, Ohio; Hisol Fast Red and Fluorescein, available from Capitol Color and Chemical Company, Newark, N.J.; and Acid Green 25, Ciba Specialty Chemicals Corporation, Greenboro, N.C.

Examples of suitable fragrances or perfumes include, but are not limited to: terpenoids such as citronellol, aldehydes such as amyl cinnamaldehyde, a jasmine such as C1S-jasmine or jasmal, and vanillin.

Use Compositions

The compositions may include concentrate compositions or may be diluted to form use compositions. In general, a concentrate refers to a composition that is intended to be diluted with water to provide a use solution that contacts a surface and/or product in need of treatment to provide the desired rinsing, sanitizing or the like. The compositions that contact the surface and/or product in need of treatment can be referred to as a concentrate or a use composition (or use solution) dependent upon the formulation employed in methods according to the invention. It should be understood that the concentration of the propoxylated surfactant or polymer and anionic surfactants and/or nonionic surfactants in the composition will vary depending on whether the composition is provided as a concentrate or as a use solution.

A use solution may be prepared from the concentrate by diluting the concentrate with water at a dilution ratio that provides a use solution having desired sanitizing and/or other antimicrobial properties. The water that is used to dilute the concentrate to form the use composition can be referred to as water of dilution or a diluent, and can vary from one location to another. The typical dilution factor is between approximately 1 and approximately 10,000 but will depend on factors including water hardness, the amount of soil to be removed and the like. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water.

In preferred embodiments the present invention includes concentrate compositions and use compositions. In an embodiment, a concentrate composition can be diluted to a use solution before applying to an object. The concentrate can be marketed and an end user can dilute the concentrate with water or an aqueous diluent to a use solution. The level of active components in the concentrate composition is dependent on the intended dilution factor and the desired activity of the antimicrobial composition. Generally, a dilution of about 1 fluid ounce to about 10 gallons of water to about 10 fluid ounces to about 1 gallon of water is used for aqueous compositions of the present invention. In some embodiments, higher use dilutions can be employed if elevated use temperature (greater than 25° C.) or extended exposure time (greater than 30 seconds) can be employed. In the typical use locus, the concentrate is diluted with a major proportion of water using commonly available tap or service water mixing the materials at a dilution ratio of about 3 to about 40 ounces of concentrate per 100 gallons of water.

In some embodiments, the concentrated compositions can be diluted at a dilution ratio of about 0.1 g/L to about 100 g/L concentrate to diluent, about 0.5 g/L to about 10.0 g/L concentrate to diluent, about 1.0 g/L to about 4.0 g/L concentrate to diluent, or about 1.0 g/L to about 2.0 g/L concentrate to diluent.

In other embodiments, a use composition can include about 0.01 to about 10 wt-% of a concentrate composition and about 90 to about 99.99 wt-% diluent; or about 0.1 to about 1 wt-% of a concentrate composition and about 99 to about 99.9 wt-% diluent.

Manufacturing Methods

Compositions of the present disclosure are prepared by simple addition of materials. In some aspects, the compositions according to the invention can be made by combining the components in an aqueous diluent using commonly available containers and blending apparatus. Beneficially, no special manufacturing equipment is required for making the compositions. A preferred method for manufacturing the cleaning composition of the invention includes introducing the components into a stirred production vessel.

Kits or Pre-Mix Formulations

In an aspect, a kit can be provided to prepare the compositions. In an aspect, a kit can include a two-part premix for a concentrated liquid composition.

In an aspect, the first part can include a propoxylated EO/PO block copolymer surfactant (or other propoxylated surfactant or polymer), and the second part can include the anionic and/or nonionic surfactant and solvents. The first part of the kit can also include a propoxylated homopolymer and/or nonionic surfactants. In an alternative aspect, the first part can include the solvent(s).

Methods of Use

The compositions provide efficacy by formulating compositions comprising various surfactant and polymer cleaning agents. The compositions further provide soil removal efficacy with enhanced foaming stability. The various methods of cleaning, soil removal, antimicrobial and/or foaming applications according to the disclosure can include the use of any suitable level of the propoxylated surfactant or polymer and additional surfactants.

The various applications of use described herein provide the active composition to a surface and/or product in need of cleaning, soil removal, anti-microbial and/or foaming soil removal. Beneficially, the compositions of the invention are fast-acting. However, the present methods require a certain minimal contact time of the compositions with the surface or product in need of treatment for occurrence of sufficient antimicrobial effect. The contact time can vary with concentration of the use compositions, method of applying the use compositions, temperature of the use compositions, pH of the use compositions, amount of the surface or product to be treated, amount of soil or substrates on/in the surface or product to be treated, or the like. The contact or exposure time can be about 15 seconds, at least about 15 seconds, about 30 seconds or greater than 30 seconds. In some embodiments, the exposure time is about 1 to 5 minutes. In other embodiments, the exposure time is at least about 10 minutes, 30 minutes, or 60 minutes. In other embodiments, the exposure time is a few minutes to hours. The contact time will further vary based upon the concentration of the actives in a use solution.

In general, the cleaning methods according to the invention involve applying the liquid cleaning composition to a surface to be cleaned, allowing the composition to remain for a sufficient period of time for cleaning (typically until any foam that is present dissipates) and thereafter rinsing said surface until that said cleaning composition is removed along with soil and debris. The surface to be cleaned can include for examples skin, namely hands of a person in need of washing thereof. In a further aspect, the surface to be cleaned can include ware.

The present methods can be conducted at any suitable temperature. In some embodiments, the present methods are conducted at a temperature ranging from about 0° C. to about 5° C., e.g., from about 5° C. to about 10° C., 0° C. to about 10° C., 0° C. to about 20° C., 0° C. to about 40° C., 0° C. to about 50° C., 0° C. to about 70° C., or at increased temperatures there above suitable for a particular application of use.

Beneficially, the compositions are suitable for antimicrobial efficacy against a broad spectrum of microorganisms, providing broad spectrum bactericidal and fungistatic activity. For example, the of this invention provide broad spectrum activity against wide range of different types of microorganisms (including both aerobic and anaerobic microorganisms, gram positive and gram negative microorganisms), including bacteria, yeasts, molds, fungi, algae, and other problematic microorganisms.

The present methods can be used to achieve any suitable reduction of the microbial population in and/or on the target or the treated target composition. In some embodiments, the present methods can be used to reduce the microbial population in and/or on the target or the treated target composition by at least one log 10. In other embodiments, the present methods can be used to reduce the microbial population in and/or on the target or the treated target composition by at least two log 10. In still other embodiments, the present methods can be used to reduce the microbial population in and/or on the target or the treated target composition by at least three log 10. In still other embodiments, the present methods can be used to reduce the microbial population in and/or on the target or the treated target composition by at least five log 10. Without limiting the scope of invention, the numeric ranges are inclusive of the numbers defining the range and include each integer within the defined range.

In an aspect, the methods of the invention include generating a use solution from the concentrated solid or liquid compositions of the invention. A use solution may be prepared from the concentrate by diluting the concentrate with water at a dilution ratio that provides a use solution having desired sanitizing and/or other antimicrobial properties. The water that is used to dilute the concentrate to form the use composition can be referred to as water of dilution or a diluent, and can vary from one location to another. The typical dilution factor is between approximately 1 and approximately 10,000. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water.

In an aspect, a concentrated composition is diluted from about 0.001% (wt/vol.) to about 10% (wt/vol.), or from about 0.001% (wt/vol.) to about 5% (wt/vol.), or from about 0.001% (wt/vol.) to about 2% (wt/vol.), or from about 0.01% (wt/vol.) to about 1% (wt/vol.). Without limiting the scope of invention, the numeric ranges are inclusive of the numbers defining the range and include each integer within the defined range.

Compositions of the invention can be formulated and sold for use as is, or as solvent or solid concentrates. If desired, such concentrates can be used full-strength as sanitizing rinse compositions. However, the concentrates typically will be diluted with a fluid (e.g., water) that subsequently forms the dilute phase or a use solution. Preferably, the concentrate forms a single phase before such dilution and remains so while stored in the container in which it will be sold. When combined with water or other desired diluting fluid at an appropriate dilution level and subjected to mild agitation (e.g., by stirring or pumping the composition), some compositions of the invention will form a pseudo-stable dispersion, and other compositions of the invention will form a clear or quasi-stable solution or dispersion. If a pseudo-stable composition is formed, then the composition preferably remains in the pseudo-stable state for a sufficiently long period so that the composition can be applied to a surface before the onset of phase separation. The pseudo-stable state need only last for a few seconds when suitably rapid application techniques such as spraying are employed, or when agitation during application is employed. The pseudo-stable state desirably lasts for at least one minute or more after mixing and while the composition is stored in a suitable vessel, and preferably lasts for five minutes or more after mixing. Often normal refilling or replenishment of the applicator (e.g., by dipping the applicator in the composition) will provide sufficient agitation to preserve the pseudo-stable state of the composition during application.

The compositions can be dosed into an application of use, or dispensed as the concentrate or use solution. The compositions can be diluted and dispensed from a dispenser.

Soaking Compositions

In one embodiment, the present invention is a foaming detergent composition which can be used as a soaking composition. The soaking composition and methods of using the soaking composition remove grease and food soils from surfaces without significant corrosive or detrimental effects on the aesthetics of such surfaces. In addition to loosening greasy, baked on soils, the soaking solution also protects the surface of the ware both while soaking in the soaking composition. The soaking composition is used to loosen grease and food soils on ware, such as pots and pans, before the pots and pans are run through a dish machine. The soaking step reduces the number of washes soiled ware must undergo to remove the soils when compared to not using a soaking composition, soaking with water, or soaking with a manual detergent. The soaking composition can be used on ware made of various materials, including, for example: stainless steel, aluminum, cast iron and plastics. The soaking composition loosens grease and soil from the surface such that the soil is substantially removed from the surface when the ware is passed through a single cycle of a dish machine. In addition, no personal protective equipment is needed when the soaking composition is used at the recommended concentration and with the recommended procedures.

Typically, when ware is soaked in a solution and then removed and placed into a dish machine, a small quantity of the soaking solution is carried with the ware. Because the soaking composition is used prior to placing the ware in a dish machine for cleaning, components in the soaking composition may produce foam. The soaking composition is formulated to produce lower foam than typical pot and pan detergents when agitated. However, beneficially according to the invention a stable foam is produced, including in the presence of food soils. As referred to herein, stable foam is a foam that remains for several minutes after agitation is stopped, in an aspect for at least 5 minutes, or at least 4 minutes, or at least 3 minutes, or at least 2 minutes, or at least 1 minute. A partially stable foam breaks slowly within a minute. An unstable foam breaks rapidly in less than 15 seconds. A antimicrobial hand soap should have stable foam.

Hand Soaps and Detergents

The composition according to the disclosure are further useful for hand soaps and detergents that provides a desired level of foaming and cleaning properties when diluted to a use solution. In various embodiments of the invention the foaming cleaning compositions of the invention can advantageously be formulated to be cocamide DEA free, phosphate-free and/or aminocarboxylate-free, as well as containing only ingredients generally recognized as safe (GRAS) for human use.

A novel cleaning method is also within the invention and involves applying the foaming cleaning compositions described in the present disclosure to a surface to be cleaned, allowing the foam to remain for a sufficient period of time for cleaning (typically until the foam dissipates) and thereafter rinsing said surface to that said cleaning composition is removed along with soil and debris.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Materials used in the following Examples are provided herein:

Glucopon 625 UP: 50% active alkyl polyglucoside nonionic surfactant

Barlox 12: cocoamine oxide nonionic surfactant (30% active lauryl dimethyl amine oxide)

Steol CS-460: 60% active sodium lauryl ether sulfate (SLES) anionic surfactant

Pluronic P84: EO-PO block co-polymer, 60% PO, 40% E0, 4000 MW (g/mol)

Pluronic L64: EO-PO block co-polymer, 60% PO, 40% E0, 3000 MW (g/mol)

Lutensol XP80: alkyl polyethylene glycol ether based on C10-Guerbet alcohol and ethylene oxide Surfonic L24-7: 7 mole ethoxylate of linear, primary 12-14 carbon alcohol Pluronic F88: EO-PO block co-polymer, 20% PO, 80% EO, 12,000 MW (g/mol)

Pluronic 25R4: EO-PO block co-polymer, 60% PO, 40% EO, 12,500 MW (g/mol)

Pluronic 17R4: EO-PO block co-polymer, 60% PO, 40% EO, 8500 MW (g/mol)

Pluronic F77: EO-PO block co-polymer, 30% PO, 70% EO, 7000 MW (g/mol)

Variquat CC 42: CAS 68132-96-7, Poly[oxy(methy-1,2-ethanediyl)], alpha-[2-diethylmethylammonio)ethyl]-omega-hydroxy chloride, quaternary ammonium compound Pluronic F98: EO-PO block co-polymer, 20% PO, 80% EO, 13,5000 MW (g/mol)

Pluronic F87: EO-PO block co-polymer, 30% PO, 70% EO, 8000 MW (g/mol)

PT1000 TB: polypropylene glycol (PPG-17), 1000 MW

Example 1

Viscosity of the evaluated formulations were measured after about 20 minutes of mixing using a Brookfield viscometer (model RVT or LVT) with spindle #2 at 50 rpm and at ambient (about 19° C.). The evaluated formulation containing the propoxylated material is shown in Table 2.

TABLE 2

| Formulation Concentration | Components | Wt-% |
|---|---|---|
| 1 × (24.5% actives) | Soft water (0 gpg) | 50-60 |
| | Glucopon 625 (50%) | 10-15 |
| | Barlox 12 (30%) | 15-20 |
| | Steol CS (60%) | 15-20 |
| | Pluronic P84 | 5-7 |
| 1.5 × (36.75% actives) | Soft water (0 gpg) | 30-50 |
| | Glucopon 625 (50%) | 15-20 |
| | Barlox 12 (30%) | 20-25 |
| | Steol CS (60%) | 25-30 |
| | Pluronic P84 | 5-10 |
| 1.75 × (42.875% actives) | Soft water (0 gpg) | 15-25 |
| | Glucopon 625 (50%) | 15-20 |
| | Barlox 12 (30%) | 25-30 |
| | Steol CS (60%) | 25-30 |
| | Pluronic P84 | 5-10 |
| 2 × (49% actives) | Soft water (0 gpg) | 5-10 |
| | Glucopon 625 (50%) | 20-25 |
| | Barlox 12 (30%) | 30-35 |
| | Steol CS (60%) | 30-35 |
| | Pluronic P84 | 10-15 |

The protocol for measuring viscosity is set forth in detail in U.S. Pat. No. 9,309,485, the entire contents of which is herein incorporated by reference in its entirety. The total actives shown for the evaluated compositions are a combination of the four compounds of each formulation and at an increasing actives level, to determine at which point the formulations become too viscous and no longer managed by the propoxylated surfactant/polymer and surfactant combinations in the composition. The measurements for viscosity according to the Brookfield viscometer specifications are <1000 cps. The target viscosity for the evaluation is between 550 cPs to 900 cPs. The results are shown in Table 3.

TABLE 3

|  | Pluronic P84 |  | Lutensol XP80 Comparative Example |  | Surfonic L24-7 Comparative Example |
|---|---|---|---|---|---|
| 1× (24.5%) | Not tested | 1× (24.5%) | 274.4 | 1× (24.5%) | Not tested |
| 1.5× (36.75%) | 700.0 | 1.5× (36.75%) | paste | 1.5× (36.75%) | paste |
| 1.75× (42.875%) | 571.2 | 1.75× (42.875%) | paste | 1.75× (42.875%) | paste |
| 2× (49%) | 489.6 | 2× (49%) | 578.8 | 2× (49%) | paste |

As shown, at increasing concentrations of the Pluronic P84 evaluated formulations the propoxylated copolymer has an increased role in maintaining viscosity. As the compositions with anionic/nonionic surfactant concentrations increase the viscosity will increase (ultimately becoming a paste where the composition is not manageable) which is primarily due to the surfactant concentration; however, beneficially according to the invention the inclusion of the propoxylated copolymer reduces the propensity for the viscoelasticity. This is distinct from the comparative formulations evaluated; namely the Lutensol XP80 which is an alcohol ethoxylate nonionic surfactant instead of the propoxylated copolymer Pluronic P84, and the Surfonic L24-7 which is also an alcohol ethoxylate nonionic surfactant instead of the propoxylated copolymer Pluronic P84.

Accordingly, there is a benefit of a significant viscosity reduction, resulting in ability of highly concentrated formulations according to the present disclosure. In an aspect, detergents formulated with high level of nonionic and anionic surfactants can become viscous, however the combination according to the present disclosure overcomes any gelling concerns and provides ease of manufacturing. Beneficially, the lowered viscosity also allows for the development of highly concentrated formulations.

Example 2

Manual Foam Height Testing and Grease Removal was conducted to screen a manual pot and pan detergent's ability to remove grease and foam height and stability.

Grease Removal Test Procedure
SOIL FORMULA:
85.5% Mazola Corn Oil (commercially available corn oil)
10% EcoSoya PB partially hydrogenated soy wax flakes
4.5% Precirol ATO 5 (glyceryl distearate)
Materials:
Overhead mixer with ability to set rpm
Constant temperature water bath or heating chamber
1000 ml polypropylene breakers
Dish rack for drying
Equipment Setup:
1. The lightning rod mixers need to be calibrated to 210 rpm. The rpm are determined with a digital readout tachometer.
2. The blade of the mixer should be centered on the 250 ml line of the beaker.
Calculations:

$$\% \text{ Removal} = \frac{\text{Soil Removed} \times 100}{\text{Total Soil}}$$

Procedure:
Mix and heat the above mixture until clear. Maintain the temperature between 154-162° F. (65-69° C.) with agitation until all beakers have been soiled. Temperature of the soil should not exceed 165° F. (74° C.). Soil (15 grams) is applied to 1000 ml polypropylene beakers which are then immersed in an ice bath. The soil solidifies and is held in the bath for five minutes. The soiled beaker is then stored at room temperature for 24 hours before performing the soil removal test. A test solution (500 ml) is heated to 105.8° F. (41° C.) in a heating chamber or water bath prior to running the removal test. The beaker is drained, held overnight in an inverted position and is reweighed. Place 500 mls of test solution in each beaker and agitate with overhead mixer set to 210 rpm for 15 minutes. After 15 minutes is complete, drain the test solution and place the beakers upside-down on a dish rack and allow to dry overnight. The next day, reweigh polypropylene beakers and calculate percent grease removal. A commercially available hand dish washing detergent can be used a control.

The following formulations were evaluated for grease removal and all tested at 1% active surfactants level:

Commercial Product 1 (CP1): competitive detergent pot and pan composition—solvents, nonionic surfactant, anionic surfactant and other agents (dye, fragrance, preservative, enzyme)

Commercial Product 2 (CP2): commercially-available detergent composition-solvents, nonionic surfactant, anionic surfactant based formula and other agents (dye, fragrance, preservative)

Base evaluated formulations are shown in Table 4.

TABLE 4

| Formulation Concentration | Components | Wt-% |
|---|---|---|
| Variquat formulations | Soft water (0 gpg) | 50-60 |
|  | Glucopon 625 (50%) | 10-15 |
|  | Barlox 12 (30%) | 15-20 |
|  | Variquat CC42 | 5-10 |
|  | SLES | 15-20 |
| Pluronic formulations | Soft water (0 gpg) | 50-60 |
|  | Glucopon 625 (50%) | 10-15 |
|  | Barlox 12 (30%) | 15-20 |
|  | Pluronics | 5-10 |
|  | SLES | 15-20 |

Grease removal results. The grease removal of commercial products compared to the based evaluated formulation were evaluated using EcoSoya PB (10%) soil solution.

Table 5 and FIG. 1 show testing results in the beakers at a 1% active surfactant level. As shown various propoxylated polymers were screened for efficacy in comparison to the commercially-available detergent formulations.

TABLE 5

| Formula | Initial Weight | Soiled Weight | Cleaned Weight | % Removal |
|---|---|---|---|---|
| CP2 | 52.28 | 67.6 | 54.86 | 83.15926893 |
| CP2 | 51.7 | 67.12 | 56.12 | 71.33592737 |
| CP2 | 53.19 | 68.42 | 56.85 | 75.96848326 |
| CP1 | 50.98 | 66.45 | 53.48 | 83.83968972 |
| CP1 | 52.32 | 67.6 | 54.13 | 88.15445026 |
| CP1 | 51.88 | 67.1 | 55.9 | 73.58738502 |
| Pluronic F88 | 51.39 | 66.87 | 60.14 | 43.4754522 |
| Pluronic F88 | 52.66 | 67.92 | 63.31 | 30.20969856 |

TABLE 5-continued

| Formula | Initial Weight | Soiled Weight | Cleaned Weight | % Removal |
|---|---|---|---|---|
| Pluronic F88 | 52.38 | 67.69 | 58.08 | 62.76943174 |
| Pluronic 25R4 | 52.26 | 67.66 | 58.48 | 59.61038961 |
| Pluronic 25R4 | 52.14 | 67.6 | 62.57 | 32.53557568 |
| Pluronic 25R4 | 52.27 | 67.48 | 56.37 | 73.04404997 |
| Pluronic 17R4 | 52.12 | 67.48 | 61.01 | 42.12239583 |
| Pluronic 17R4 | 50.77 | 66.09 | 61.97 | 26.89295039 |
| Pluronic 17R4 | 50.73 | 66.14 | 55.02 | 72.16093446 |
| Pluronic F77 | 52.44 | 67.72 | 64.21 | 22.97120419 |
| Pluronic F77 | 52.71 | 68.15 | 63.14 | 32.44818653 |
| Pluronic F77 | 50.83 | 66.13 | 63.42 | 17.7124183 |
| Variquat CC42 | 52.01 | 67.43 | 62.7 | 30.67444877 |
| Variquat CC42 | 50.93 | 66.18 | 51.76 | 94.55737705 |
| Variquat CC42 | 51.37 | 66.75 | 58.67 | 52.53576073 |

Figure 2:
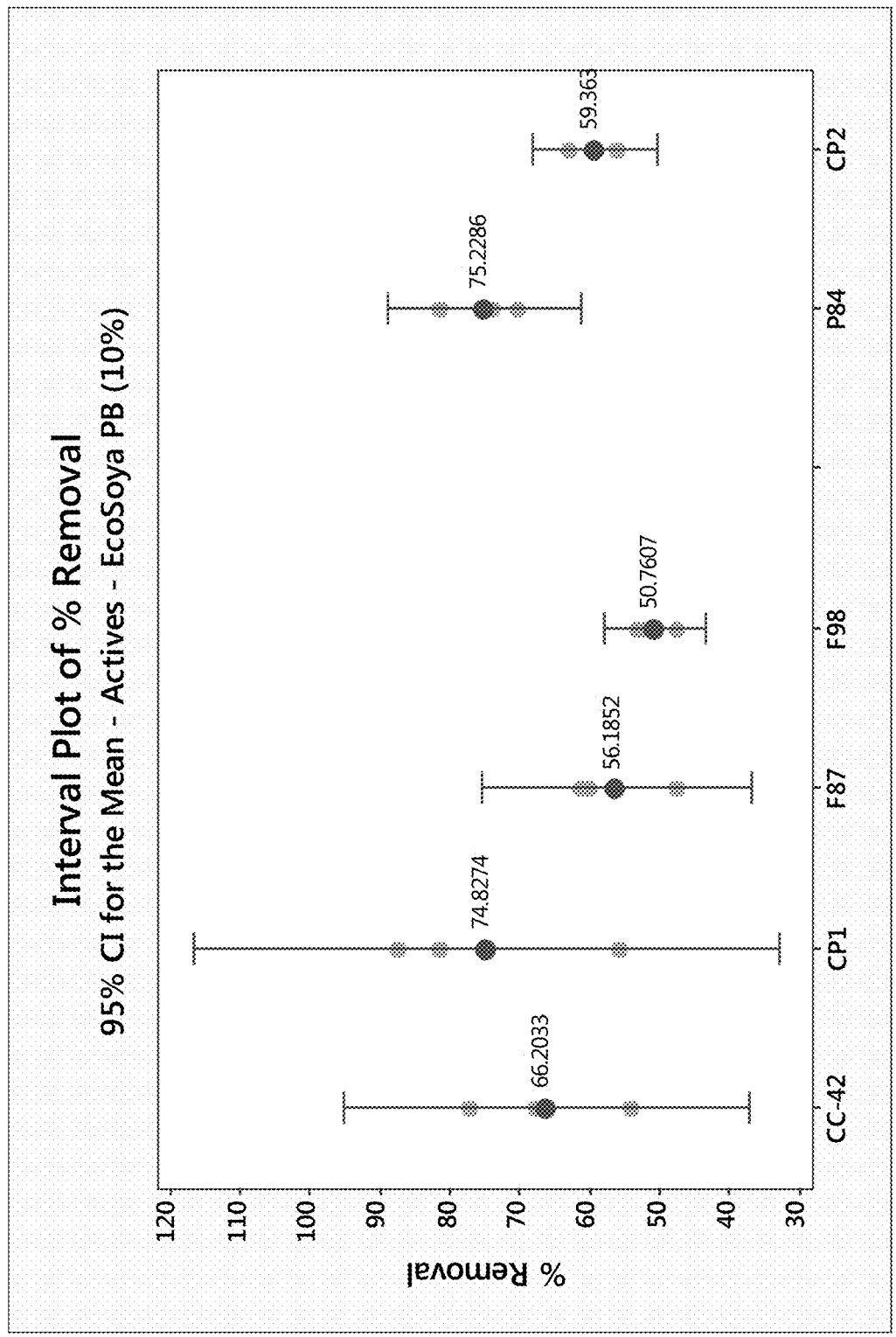
FIG. 2 shows an interval plot of the percentage of soil removal using various commercial controls (antimicrobial compositions) and compositions containing non-propoxylated surfactants compared to compositions containing propoxylated surfactants or polymers.

Table 6 and FIG. 2 shows additional testing with distinct propoxylated copolymers in comparison to the commercial controls and non-propoxylated formulations at a 1% active surfactant level. The ability to provide soil removal efficacy at least consistent with the commercially-available detergent compositions was observed.

TABLE 6

| Formula | Initial Weight | Soiled Weight | Cleaned Weight | % Removal |
|---|---|---|---|---|
| CP2 | 51.31 | 66.62 | 57.57 | 59.1116917 |
| CP2 | 53.15 | 68.57 | 58.85 | 63.03501946 |
| CP2 | 51.35 | 66.58 | 58.06 | 55.9422193 |
| CP1 | 51.06 | 66.39 | 52.99 | 87.41030659 |
| CP1 | 52.15 | 67.52 | 55.01 | 81.39232271 |
| CP1 | 53.06 | 68.29 | 59.81 | 55.67957978 |
| Variquat CC-42 | 51.66 | 66.93 | 56.6 | 67.64898494 |
| Variquat CC-42 | 52.13 | 67.37 | 55.62 | 77.09973753 |
| Variquat CC-42 | 52.34 | 67.62 | 59.39 | 53.86125654 |
| Pluronic F98 | 51.8 | 67.05 | 59.18 | 51.60655738 |
| Pluronic F98 | 52.62 | 67.98 | 59.82 | 53.125 |
| Pluronic F98 | 51.3 | 66.61 | 59.33 | 47.55062051 |
| Pluronic F87 | 53.14 | 68.49 | 59.29 | 59.93485342 |
| Pluronic F87 | 53.36 | 68.63 | 59.26 | 61.362148 |
| Pluronic F87 | 53.31 | 68.63 | 61.39 | 47.25848564 |
| Pluronic P84 | 51.4 | 66.64 | 55.92 | 70.34120735 |
| Pluronic P84 | 50.98 | 66.35 | 54.98 | 73.97527651 |
| Pluronic P84 | 52.26 | 67.45 | 55.09 | 81.36932192 |

Table 7 shows the evaluated PO placement, ratio of PO-EO and the total molecular weight of the copolymers.

TABLE 7

| Name | % PO | % EO | Total Mw | Cloud Point 1% aq. ° C. | Ross Miles Foam (0.1% @ 50° C.) | Surface Tension (@ 0.1%) | Grease Beaker Average |
|---|---|---|---|---|---|---|---|
| Pluronic P84 | 60 | 40 | 4000 | 74 | 90 | 42 | 75.2286 |
| Pluronic F87 | 30 | 70 | 8000 | >100 | 80 | 44 | 56.1852 |
| Pluronic 25R4 | 60 | 40 | 12500 | 40 | 25 | 41 | 55.0633 |
| Pluronic F98 | 20 | 80 | 13500 | >100 | 40 | 43 | 50.7607 |
| Pluronic 17R4 | 60 | 40 | 8500 | 46 | | 44 | 47.0588 |
| Pluronic F88 | 20 | 80 | 12000 | >100 | 80 | 48 | 45.4849 |
| Pluronic F77 | 30 | 70 | 7000 | >100 | 100 | 47 | 24.3773 |

Figure 3:
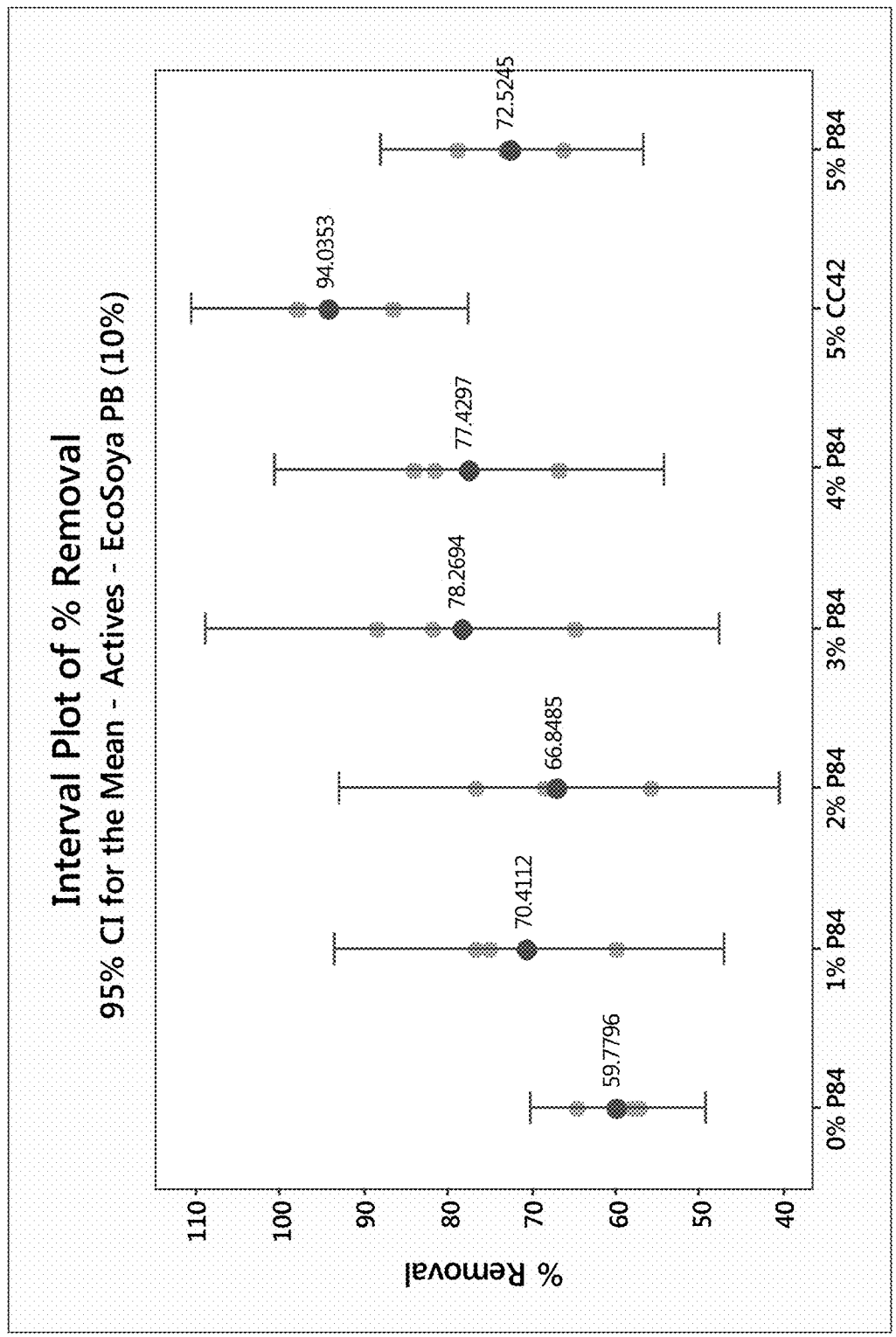
FIG. 3 shows an interval plot of the percentage of soil removal using compositions containing non-propoxylated surfactants or varying concentrations thereof compared to compositions containing propoxylated surfactants or polymers.

Table 8 and FIG. 3 show still further testing with the EcoSoya PB (10%) soil solution in the beakers with various propoxylated copolymers evaluated at varying concentrations to determine grease removal efficacy. The formulations have been previously evaluated at 5% actives, and in Table 8 formulations having from 0% to 5% were further evaluated to assess the decrease in concentration of the propoxylated surfactant. The results show that the presence of at least 1% of the propoxylated surfactant are beneficial for the efficacy and viscosity of the compositions, with concentrations of 3% to 5% preferred.

TABLE 8

| Formula | Initial Weight | Soiled Weight | Cleaned Weight | % Removal |
|---|---|---|---|---|
| 0% P84 | 52.4 | 67.66 | 58.84 | 57.79816514 |
| 0% P84 | 53.13 | 68.42 | 59.71 | 56.96533682 |
| 0% P84 | 52.33 | 67.63 | 57.75 | 64.5751634 |
| 1% P84 | 52.49 | 67.74 | 58.64 | 59.67213115 |
| 1% P84 | 52.99 | 68.2 | 56.55 | 76.59434583 |
| 1% P84 | 51.38 | 66.64 | 55.2 | 74.9672346 |
| 2% P84 | 52.4 | 67.59 | 59.14 | 55.62870309 |
| 2% P84 | 51.85 | 67.07 | 55.41 | 76.60972405 |
| 2% P84 | 52.08 | 67.32 | 56.91 | 68.30708661 |
| 3% P84 | 51.25 | 66.44 | 53 | 88.47926267 |
| 3% P84 | 52.25 | 67.47 | 55.03 | 81.73455979 |
| 3% P84 | 52.11 | 67.39 | 57.52 | 64.59424084 |
| 4% P84 | 52.68 | 68.17 | 57.83 | 66.75274371 |
| 4% P84 | 50.78 | 66.12 | 53.22 | 84.09387223 |
| 4% P84 | 53.1 | 68.35 | 55.93 | 81.44262295 |
| 5% P84 | 52.65 | 67.87 | 56.78 | 72.86465177 |
| 5% P84 | 50.94 | 66.46 | 56.21 | 66.04381443 |
| 5% P84 | 50.95 | 66.23 | 54.21 | 78.66492147 |

Figure 4:
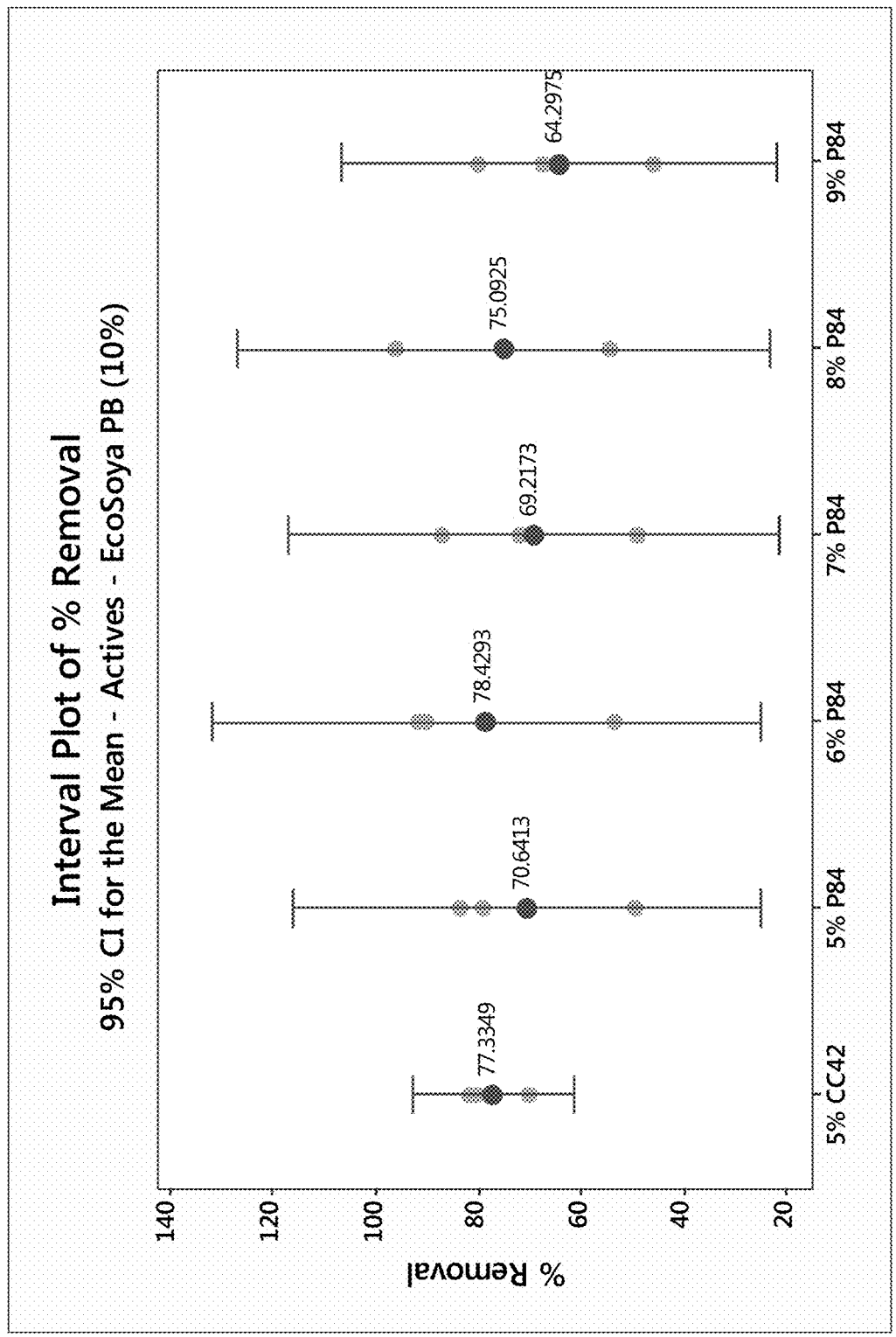
FIG. 4 shows an interval plot of the percentage of soil removal using compositions containing non-propoxylated surfactants or varying concentrations thereof compared to compositions containing propoxylated surfactants or polymers.

Table 9 and FIG. 4 show still further testing with the EcoSoya PB (10%) soil solution in the beakers with various propoxylated copolymers evaluated at varying concentrations in the formulations to determine grease removal efficacy. The formulations have been previously evaluated at 0% to 5% actives, and in Table 9 formulations having from 5% to 9% were further evaluated to assess the increase in concentration of the propoxylated surfactant. The results show that the presence of the propoxylated surfactant at all evaluated concentrations is beneficial for the efficacy and viscosity of the compositions.

TABLE 9

| Formula | Initial Weight | Soiled Weight | Cleaned Weight | % Removal |
|---|---|---|---|---|
| 6% P84 | 52.34 | 67.61 | 59.42 | 53.6345776 |
| 6% P84 | 50.97 | 66.15 | 52.24 | 91.63372859 |
| 6% P84 | 50.76 | 66.09 | 52.29 | 90.01956947 |
| 7% P84 | 52.28 | 67.5 | 60.06 | 48.88304862 |
| 7% P84 | 51.02 | 66.28 | 52.99 | 87.0904325 |
| 7% P84 | 50.99 | 66.42 | 55.36 | 71.67854828 |
| 8% P84 | 51.85 | 67.16 | 52.43 | 96.21162639 |
| 8% P84 | 52.78 | 68.02 | 59.71 | 54.52755906 |
| 8% P84 | 52.33 | 67.49 | 56.19 | 74.53825858 |
| 9% P84 | 52.72 | 67.94 | 60.95 | 45.92641261 |
| 9% P84 | 51.44 | 66.67 | 54.53 | 79.71109652 |
| 9% P84 | 51.4 | 66.7 | 56.41 | 67.25490196 |
| 5% P84 | 51.94 | 67.02 | 59.55 | 49.53580902 |
| 5% P84 | 52.4 | 67.65 | 54.95 | 83.27868852 |
| 5% P84 | 51.47 | 66.74 | 54.66 | 79.10936477 |

Example 3

Cylinder foam testing was conducted using a range of propoxylated surfactant Pluronic P84 at 1%, 5% and 9% actives. A soil formula as follows was utilized: 45% Crisco Shortening, 30% Flour, 15% Powdered Egg, and 10% Oleic acid.

Test procedure: To a 250 ml graduated cylinder, 40 mls of test solution was added and the step repeated for each product. All cylinders were labeled and brought to room temperature to avoid excess foam heights. The soil was liquified by placing on a hot plate at 200 F to form a homogenous liquid (for unifer drops of soil to be added to the cylinders). Cylinders were secured tightly and rotated at 30 rpm for 240 seconds (4 minutes). Then the initial foam height was recorded. 2 drops (0.5 g) soil were added with disposable pipettes. Then the cylinder was rotated at 30 rpm for 120 seconds (2 minutes) and foam height was again recorded. The steps of adding 2 drops (0.5 g) soil with disposable pipette were repeated until 40 mls or less foam height remained.

Calculations: To characterize each composition's performance by a single number, take the sum of all foam heights and subtract 40 mL from each reading as follows:

$$\text{Total Foam Height} = \sum \left( \begin{array}{c} \text{Individual} \\ \text{Foam Heights} \end{array} \right) - \left( \begin{array}{c} \text{Number of} \\ \text{Foam Heights} \end{array} \right) \cdot 40 \text{ mL}$$

The results are shown in Table 10.

TABLE 10

| P84% | Grease Beaker Average Equal Actives (1%) | Cylinder Foam Total Equal Actives (500 ppm) |
|---|---|---|
| 6 | 78.4293 | Not tested |
| 3 | 78.2694 | Not tested |
| 4 | 77.4297 | Not tested |
| 8 | 75.0925 | Not tested |
| 5 | 72.7981 | 795 |
| 1 | 70.4112 | 855 |
| 7 | 69.2173 | Not tested |
| 2 | 66.8485 | Not tested |
| 9 | 64.2975 | 800 |
| 0 | 59.7796 | Not tested |

Example 4

An additional type of propoxylated polymer was evaluated according to the protocol set forth in Example 1. PT1000 TB, a polypropylene glycol, from Dow Chemical was evaluated according to the formulation in Table 11.

TABLE 11

| Formulation Concentration | Components | Wt-% |
|---|---|---|
| PT1000TB formulations | Soft water (0 gpg) | 50-60 |
| | Glucopon 625 (50%) | 10-15 |
| | Barlox 12 (30%) | 15-20 |
| | PT1000TB PO polymer (no EO) | 5-10 |
| | SLES | 15-20 |

The viscosity results are shown in Table 12.

TABLE 12

| | 5% PT1000TB |
|---|---|
| 1 × (24.5%) | |
| 1.5 × (36.75%) | 147.2 |
| 1.75 × (42.875%) | 164.8 |
| 2 × (49%) | not stable |

The results show that the PO containing solvent does not provide the same surfactancy as the propoxylated EO/PO copolymer surfactants according to the preferred compositions described herein. However, there remain benefits to formulate a PO containing solvent to impact the viscoelasticity of a formulation.

Example 5

Based on the evaluated formulations of Table 5, additional formulations were evaluated with replacement solvents instead of water for the grease removal compositions. The formulations are shown in Table 13 having varying amounts of the solvents propylene glycol and hexylene glycol.

TABLE 13

| Description | All PG | All HG | 1:1 PG:HG | 2:1 PG:HG | 3:1 PG:HG |
|---|---|---|---|---|---|
| Propylene Glycol | 10-12 | | 5-7 | 7-10 | 7-10 |
| Hexylene Glycol | | 10-12 | 5-7 | 2-5 | 2-5 |
| Barlox 12 (30%) | 20-30 | 20-30 | 20-30 | 20-30 | 20-30 |
| Glucopon 625 UP (50%) | 15-25 | 15-25 | 15-25 | 15-25 | 15-25 |
| Pluronic L64 | 10-15 | 10-15 | 10-15 | 10-15 | 10-15 |
| SLES (70%) | 25-30 | 25-30 | 25-30 | 25-30 | 25-30 |
| Optional Ingredients (acidulant, preservative) | to 100 | to 100 | to 100 | to 100 | to 100 |
| TOTAL | 100 | 100 | 100 | 100 | 100 |
| ACTIVES | 49 | 49 | 49 | 49 | 49 |

The formulations were evaluated at a 2X (49% actives) formulation of those in Table 13. The viscosity (cPs) at room temperature and at 40'F were measured along with the total cylinder foam (mL) and results are shown in Table 14.

TABLE 14

| Description | All PG | All HG | 1:1 PG:HG | 2:1 PG:HG | 3:1 PG:HG |
|---|---|---|---|---|---|
| RT VISC (cPs) (#2, 50 RPM) | 610.4 | 186.4 | 300 | 376 | 424 |
| 40F VISC (cPs) (#3 or 4, 50 RPM) | 1768 | 501.6 | 850 | 1084 | 1170 |
| TOTAL CYLINDER FOAM (ML) | 1073 | 1083 | 1023 | 973 | 951 |

The protocol for measuring viscosity is set forth in detail in Example 1. The total actives (49%) shown for the evaluated compositions are a combination of the entire formulation to assess whether the highly concentrated formulations (49% actives) are too viscous and no longer managed by the propoxylated surfactant/polymer and surfactant combinations in the composition. The target viscosity for the evaluation is between 550 cPs to 900 cPs. However, as one skilled in the art will ascertain certain formulations having a viscosity greater than 900 cPS can be employed with modifications to the dosing or dispensing, such as adjustment to the aspirator (e.g. larger dispensing tip).

As shown in Table 13, all evaluated formulations met the viscosity thresholds at room temperature. The formulations having All HG and 1:1 PG:HG met the viscosity thresholds at both room temperature and 40 F. However, as one skilled in the art will ascertain certain, dependent upon the desired application of use conditions (e.g. the temperature) the solvents could be adjusted—namely the ratio of solvents—to provide the desired viscosity of less than 900 cPS at a preferred temperature, such as room temperature or 40 F (4 C).

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A kit comprising:
   a two-part premix for a concentrated liquid composition comprising a first part and a second part;
   wherein the first part comprises propoxylated surfactant comprising an ethylene oxide/propylene oxide (EO/PO) block copolymer surfactant in an amount of between about 1 wt-% to about 50 wt-% of the concentrated liquid composition;
   wherein the second part comprises an anionic surfactant and at least one-nonionic surfactant in an amount of at least about 20 wt-% of the concentrated liquid composition, and solvent(s); and
   wherein the concentrated liquid composition has a viscosity of less than about 900 cPs and does not include ethanol.

2. The kit of claim 1, wherein the first part further comprises a propoxylated homopolymer.

3. The kit of claim 1, wherein the solvent(s) comprises propylene glycol and/or hexylene glycol.

4. The kit of claim 1, wherein the solvent(s) are present in an amount of between about 1 wt-% and about 30 wt-% of the concentrated liquid composition.

5. The kit of claim 1, wherein the EO/PO block copolymer surfactant has the following structure $(EO)_n(PO)_m(EO)_n$ or $(PO)_m(EO)_n(PO)_m$, wherein n is the average number of polymerized ethylene oxide units and m is the average number of polymerized propylene oxide units, and wherein the molecular weight is between about 1000 g/mol and about 15,000 g/mol and with a Ross Miles Foam of greater than or equal to 40 (0.1% @ 50° C.).

6. The kit of claim 1, wherein the EO/PO block copolymer surfactant has a molecular weight of at least about 3000 g/mol.

7. The kit of claim 1, wherein the first part further comprises a propoxylated polymer or copolymer comprising one or more of: propoxylated homopolymer; polyethyleneimine derivative propoxylated polymer having a PO group, EO-PO group or PO-EO group; or an extended chain surfactant.

8. The kit of claim 7, wherein the extended chain surfactant (a) has the formula R—[L]x—[O—CH$_2$—CH$_2$]y, wherein R is the lipophilic moiety, a linear or branched, saturated or unsaturated, substituted or unsubstituted, aliphatic or aromatic hydrocarbon radical having from about 8 to 20 carbon atoms, L is a linking group comprising a block of poly-propylene oxide, a block of poly-ethylene oxide, a block of poly-butylene oxide or a mixture thereof; x is the chain length of the linking group ranging from 2-25; and y is the average degree of ethoxylation ranging from 1-20, and/or (b) is an extended chain anionic surfactant and has the formula R—[L]x—[O—CH$_2$—CH$_2$]y M, wherein R is the lipophilic moiety, a linear or branched, saturated or unsaturated, substituted or unsubstituted, aliphatic or aromatic hydrocarbon radical having from about 8 to 20 carbon atoms, L is a linking group comprising a block of polypropylene oxide, a block of poly-ethylene oxide, a block of poly-butylene oxide or a mixture thereof; x is the chain length of the linking group ranging from 1-15; y is the average degree of ethoxylation ranging from 1-5, and M is any ionic species.

9. The kit of claim 7, wherein the propoxylated homopolymer is polypropylene glycol and does not provide surfactant activity.

10. The kit of claim 1, wherein the first part further comprises the solvent(s).

11. The kit of claim 1, wherein the anionic surfactant is a C6-C18 alkyl chain length linear or branched carboxylate, sulfate, sulfonate, or a mixture thereof.

12. The kit of claim 1, wherein the anionic surfactant is comprised of sodium lauryl ether sulfate, sodium lauryl sulfate, alpha olefin sulfonate, alkylbenzene sulfonic acid, or a mixture thereof.

13. The kit of claim 1, wherein the nonionic surfactant is an alcohol ethoxylate, alcohol alkoxylate, block copolymer, amine oxide, alkylpolyglucoside, or a combination thereof.

14. The kit of claim 1, wherein the concentrated liquid composition further comprises water and/or one or more additional functional ingredients comprising additional surfactants, solubility modifiers, humectants, metal protecting agents, stabilizing agents, corrosion inhibitors, sequestrants and/or chelating agents, preservatives, sheeting agents, pH modifying components, fragrances and/or dyes, hydrotropes or couplers, and/or buffers.

15. The kit of claim 1, wherein the concentrated liquid composition has an active concentration of at least about 18%.

16. The kit of claim 1, wherein the concentrated liquid composition has an active concentration of at least about 30% and has a viscosity less than about 500 cPs.

17. The kit of claim 1, wherein the concentrated liquid composition further comprises an antimicrobial agent and provides at least a 3 log microbial kill on a treated surface.

* * * * *